(12) United States Patent
Nozaki et al.

(10) Patent No.: US 7,360,462 B2
(45) Date of Patent: Apr. 22, 2008

(54) METHOD AND EQUIPMENT FOR INSPECTING REINFORCED CONCRETE PIPE

(75) Inventors: Yoshiharu Nozaki, Kyoto (JP); Takushi Minagi, Kyoto (JP)

(73) Assignee: Sekisui Chemical Co., Ltd., Kyoto (JP)

( * ) Notice: Subject to any disclaimer, the term of this patent is extended or adjusted under 35 U.S.C. 154(b) by 0 days.

(21) Appl. No.: 10/513,698

(22) PCT Filed: Apr. 10, 2003

(86) PCT No.: PCT/JP03/04587

§ 371 (c)(1),
(2), (4) Date: Nov. 8, 2004

(87) PCT Pub. No.: WO03/096007

PCT Pub. Date: Nov. 20, 2003

(65) Prior Publication Data

US 2005/0172697 A1    Aug. 11, 2005

(30) Foreign Application Priority Data

May 8, 2002   (JP)   ............... 2002-133022
Oct. 11, 2002  (JP)   ............... 2002-299179

(51) Int. Cl.
    *G01N 29/34*   (2006.01)
(52) U.S. Cl. ................. 73/865.8; 73/584; 73/588; 73/592
(58) Field of Classification Search ........... 73/584, 73/588, 592, 865.8
    See application file for complete search history.

(56) References Cited

U.S. PATENT DOCUMENTS

| | | | | |
|---|---|---|---|---|
| 4,177,798 A | * | 12/1979 | Leveque et al. | 600/587 |
| 4,233,849 A | * | 11/1980 | Defebvre et al. | 73/812 |
| 4,342,229 A | * | 8/1982 | Massa | 73/579 |

(Continued)

FOREIGN PATENT DOCUMENTS

| | | | |
|---|---|---|---|
| JP | 60-207013 | | 10/1985 |
| JP | 62006164 A | * | 1/1987 |
| JP | 62-34360 | | 2/1987 |
| JP | 62-98287 | | 5/1987 |
| JP | 6-331610 | | 12/1994 |
| JP | 7-20097 | | 1/1995 |
| JP | 10-73573 | | 3/1998 |
| JP | 2001-141660 | | 5/2001 |
| JP | 2001-349876 | | 12/2001 |
| JP | 2002-115491 | | 4/2002 |

OTHER PUBLICATIONS

Minaki et al., "Fundamental Research Relating to Method of Diagnosing Degradation of Concrete Drainage Pipelines Using Elastic Waves", Annual Papers of the Concrete Industry, vol. 24, No. 1 (2002), pp. 1539-1544.*

*Primary Examiner*—Hezron Williams
*Assistant Examiner*—David A. Rogers
(74) *Attorney, Agent, or Firm*—Wenderoth, Lind & Ponack, L.L.P.

(57) ABSTRACT

Deterioration of reinforced concrete pipes is checked and the deterioration progress level is classified. Based on the inspection result, a portion to be inspected in detail in an inspection area is selected. With respect to the selected portion to be inspected in detail, the pipe thickness and the diameter of reinforcing bars are measured and the location of reinforcing bars in the portion to be inspected in detail are checked. Using the data of the thickness of a pipe, the diameter of the reinforcing bar and disposition of the reinforcing bars, structural analysis is carried out and the strength of the reinforced concrete pipe is calculated. The calculation result is used as information for evaluating the deterioration state of the reinforced concrete pipe.

1 Claim, 22 Drawing Sheets

U.S. PATENT DOCUMENTS

| | | | |
|---|---|---|---|
| 4,603,584 A * | 8/1986 | Bartle et al. | 73/599 |
| 4,697,456 A * | 10/1987 | Maser | 73/592 |
| 4,702,111 A * | 10/1987 | Holland | 73/579 |
| 4,858,469 A * | 8/1989 | Hosgood et al. | 73/579 |
| 5,048,320 A * | 9/1991 | Mitsuhashi et al. | 73/12.09 |
| 5,144,838 A * | 9/1992 | Tsuboi | 73/579 |
| 5,165,270 A * | 11/1992 | Sansalone et al. | 73/12.08 |
| 5,571,966 A * | 11/1996 | Tsuboi | 73/579 |
| 5,992,234 A * | 11/1999 | Rhodes et al. | 73/579 |
| 6,751,560 B1 * | 6/2004 | Tingley et al. | 702/51 |
| 6,785,616 B2 * | 8/2004 | Lung et al. | 702/34 |

* cited by examiner

Load-stress curve

Hume pipe cutting procedure

Crack introducing method

→ Top peak in frequency range of 4 to 10kHz
⇒ Top peak in frequency range of 3 to 4kHz Resonant frequency spectrum of sample T54

Resonant frequency spectrum of sample T55

↓ Top peak in a frequency range of 4 to 10kHz

↓ Top peak in a frequency range of 3 to 4kHz

FIG. 31

| Example 7-1 | Example 7-2 | Example 7-3 | Comparison example 7-1 |
|---|---|---|---|
| circular cone | pyramid-like shape | spherical | cylindrical |
| 15mm × 15mm, 10mm | 15mm × 15mm, Front end area 1.77cm² | 30mm φ Spherical surface, 15mm × 15mm, 5mm | 20mm × 15mm, Front end area 3.14cm² |

Measurement results of sample of pipe with reduced thickness

Measurement results of sample applied with lard

METHOD AND EQUIPMENT FOR INSPECTING REINFORCED CONCRETE PIPE

TECHNICAL FIELD

The present invention relates to an inspection method and an inspection apparatus for inspecting the deterioration state of reinforced concrete pipes.

BACKGROUND ART

Conventionally, in a sewage conduit and irrigation conduit, many reinforced concrete pipes (Hume pipe) are used.

In sewage and irrigation conduits built using reinforced concrete pipes, due to corrosion, abrasion and breakage caused from aging of concrete pipes, problems such as cave-in and water leakage have been increasing. Therefore, appropriate repair and renewal thereof based on appropriate diagnosis of the deterioration and the inspection result thereof are required.

In the diagnosis and inspection of the sewage and irrigation conduits, generally, in order to determine the order and construction method of repair and renewal work, it is required to classify the progression level of deterioration in a component segment constituting the drainage basin to be inspected, and it is necessary to detect the progression level of the deterioration in a quantitative manner.

Conventionally, in general, such a method, in which a visual check and an appearance inspection are carried out using a TV camera; and if necessary, a core is taken out to inspect solid state properties thereof, is carried out.

However, in the above-mentioned technique, only visible deterioration can be detected; accordingly, deterioration on the periphery and inside of the pipe cannot be detected. Additionally, it is impossible to detect the progression level of deterioration in an appropriate and quantitative manner, and it is necessary to take out a large amount of cores to collect quantitative data. Therefore, there arise such problems that the strength of the sewage or irrigation conduit is reduced, and significant manpower is required.

On the other hand, it has been considered to put the inspection methods used for concrete structures into use.

For example, systems, in which the width and depth of cracks are estimated using elastic waves, have been disclosed in Japanese Published Unexamined Patent Application No. H10-142200 and Japanese Published Unexamined Patent Application No. H09-269215. However, these systems are not satisfactory in workability. When these systems are applied to the inspection of a structure extending over a long distance such as sewage and irrigation conduits, it takes a considerably long time for the inspection.

The present invention has been proposed to solve the above-described problems. It is an object of the present invention to provide an inspection method for reinforced concrete pipes which, when inspecting the deterioration state of a reinforced concrete pipe constituting a sewage conduit, irrigation conduit or the like, is capable of increasing the efficiency of the inspection work as well as evaluating the progression level of deterioration in a quantitative manner, and an inspection apparatus suitable for carrying out such an inspection method.

SUMMARY OF THE INVENTION

An inspection method according to the present invention is an inspection method for reinforced concrete pipes for inspecting the deterioration state of a reinforced concrete pipe inside the pipe, which comprises an inspection step for checking the presence or absence of deterioration by carrying out any one or both of a visual examination and impact elastic wave test and classifying the progression level of the deterioration; an inspection portion selecting step for selecting a portion to be inspected in detail in an inspection area based on the inspection result; a measuring step for measuring the pipe thickness and the diameter of reinforcing bars in the selected portion to be inspected in detail; a reinforcing bar disposition checking step for checking the location of the reinforcing bars in the portion to be inspected in detail; and a calculating step for calculating the strength of the reinforced concrete pipe by analyzing the structure using the respective data of the pipe thickness, the diameter of the reinforcing bars and the disposition of the reinforcing bars obtained in those two steps. The calculation result obtained in the calculating step is used as the information for evaluating the deterioration state of the reinforced concrete pipe.

According to the inspection method of the present invention, since the progression level of the deterioration of the component segment in the area to be inspected is classified and the portion to be inspected in detail is selected, the inspection operation time can be reduced. Further, the progression level of the deterioration in the portion to be inspected in detail can be evaluated based on the strength of the pipe in a quantitative manner.

In the inspection method according to the present invention, it may be adapted so that, in addition to the pipe thickness and the diameter of the reinforcing bars, the depth of cracks is measured in the measuring process.

Further either or both of the step for determining the deteriorated portion (position of cracks) and the step for measuring the strength of concrete may be added.

In the inspection method of the present invention, it is preferred to carry out the measurement of the pipe thickness to be inspected, the determination of the deteriorated portion and the measurement of the depth of cracks using an elastic wave transmitter and receiver.

The inspection method according to the present invention is an inspection method for reinforced concrete pipes for inspecting the deterioration state of a reinforced concrete pipe inside the pipe, which comprises the steps of: measuring propagation waves of a pipe to be inspected by carrying out an impact elastic wave test; analyzing the resonant frequency spectrum of the propagation waves; and determining the deterioration level based on the area ratio between an area of a high frequency component and an area of a low frequency component in the resonant frequency spectrum.

The inspection method according to the present invention is an inspection method for reinforced concrete pipes for inspecting the deterioration state of a reinforced concrete pipe inside the pipe, which comprises the steps of: measuring propagation waves of a pipe to be inspected by carrying out an impact elastic wave test; analyzing the resonant frequency spectrum of the propagation waves; and determining the deterioration level based on the strength ratio between the top peak strength in the high frequency range (for example, frequency range of 4 to 10 kHz) and the top peak strength in the low frequency range (for example, frequency range 3 to 4 kHz) in the resonant frequency spectrum.

The inspection method according to the present invention is an inspection method for reinforced concrete pipes for inspecting the deterioration state of a reinforced concrete pipe inside the pipe, which comprises the steps of measuring propagation waves of a pipe to be inspected by carrying out an impact elastic wave test; and determining the deterioration level based on the changes in the maximum amplitude value of the propagation waves. The wording "maximum amplitude value of the propagation wave" in the present invention means the magnitude at which the absolute value in the waveform data of the propagation waves reaches the maximum value as shown in FIG. 16.

According to the respective inspection methods of the invention, the deterioration level of a reinforced concrete pipe constituting a sewage conduit, irrigation conduit or the like can be determined in a quantitative manner.

The inspection method according to the present invention is an inspection method for reinforced concrete pipes for inspecting the deterioration state of a reinforced concrete pipe inside the pipe, which comprises the steps of: measuring propagation waves by carrying out an impact elastic wave test; obtaining changes of maximum magnitude in the propagation waves; calculating the area ratio between the area of the high frequency component and the area of the low frequency component in the resonant frequency spectrum by analyzing the resonant frequency spectrum of the propagation waves; and determining the classification of deterioration phenomenon and the deterioration progress level by combining the changes of maximum amplitude value in the propagation waves and the area ratio in the resonant frequency spectrum.

In the inspection method of the invention, it may be arranged so that a step for calculating the strength ratio between the top peak strength in a high frequency range and the top peak strength in a low frequency range of the resonant frequency spectrum is added, and the determination is carried out while adding the top peak strength ratio to the determination criteria.

Also, it may be arranged so that, a step for calculating the changes in decay time of the propagation waves, and the determination is carried out while adding the changes in decay time to the determination criteria.

The inspection method according to the present invention is an inspection method for reinforced concrete pipes for inspecting the deterioration state of a reinforced concrete pipe inside the pipe by means of an impact elastic wave test. The impact elastic wave test is carried out in a state in which the distance between the elastic wave injecting position and the elastic wave receiving position is ¼ or more of the length of the pipe to be inspected away from each other.

The reason why the disposition distance is prescribed is to clearly detect the changes of the vibration mode. That is, when the distance between the elastic wave injecting position and the receiving position is shorter than ¼ of the length of the pipe, the vibrations in the area adjacent to the transmitter are detected too strongly. In addition, the changes of the vibration mode due to the deterioration in a portion far away from the elastic wave injecting position and the elastic wave receiving position is received unclearly. By setting the distance between the elastic wave injecting position and the receiving position to ¼ or more of the length of the pipe, the intended object can be achieved. More preferably, the distance is ⅓ or more of the length of the pipe.

The inspection method according to the present invention is an inspection method for reinforced concrete pipes for inspecting the deterioration state of a reinforced concrete pipe inside the pipe by means of an impact elastic wave test. The impact elastic wave test is carried out by using any one of a receiver of which the configuration of the front end is a cone-like shape or needle-like shape, a receiver of which the front end surface is a flat surface and the area of the front end surface is 3 $cm^2$ or less, or a receiver of which the front end surface is a curved surface and the curvature radius of the front end surface is 25 mm or less as the receiver of the elastic waves.

As described above, by controlling the configuration of the receiver, receiving failure of the impact elastic waves (propagation waves) due to a contact failure between the receiver and the pipe inner surface caused from adhered layers, decayed layers on the inner surface layer of the reinforced concrete pipe constituting the sewage conduit, irrigation conduit or the like, or unevenness of the surface due to exposed reinforcing bars caused from abrasion, can be eliminated. Accordingly, the accuracy of the test can be prevented from degrading.

An inspection apparatus according to the present invention is an inspection apparatus for reinforced concrete pipes used for inspecting the deterioration state of a reinforced concrete pipe inside the pipe by means of an impact elastic wave test, which comprises: a trolley mounted with a hammering unit; a trolley mounted with a receiving unit; and a joint member for connecting the two trolleys at a specific distance.

The inspection apparatus according to the present invention may be adapted so as to determine an elastic wave injecting position and elastic wave receiving position by using a trolley mounted with a TV camera.

BRIEF DESCRIPTION OF THE DRAWINGS

FIG. 31 is a diagram showing configurations of receivers used in examples of the present invention;

DETAILED DESCRIPTION OF THE INVENTION

Figure 1:
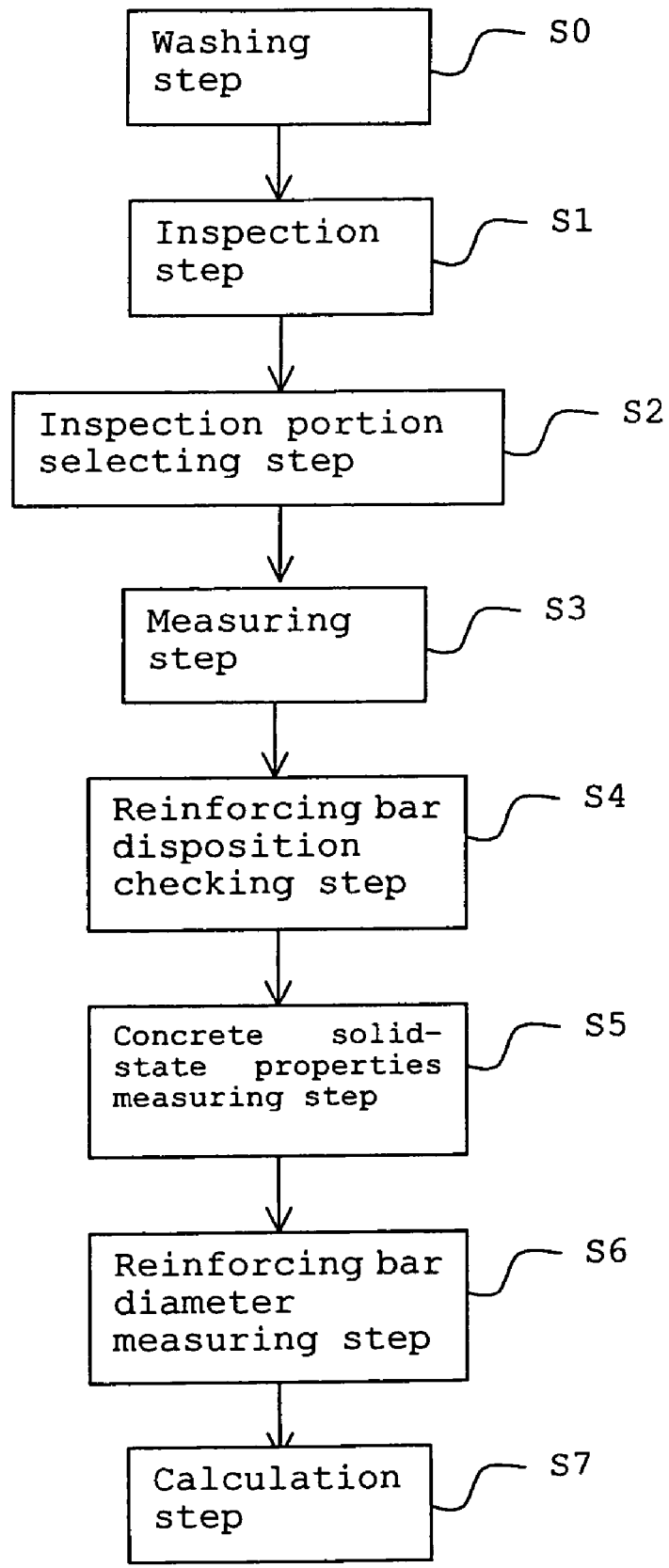
FIG. 1 is a diagram showing an inspection process according to an embodiment of the present invention.

Hereinafter, referring to the drawings, embodiments of the present invention will be described below.

Embodiment 1

An embodiment of an inspection method according to the present invention will be described step by step with reference to FIG. 1.

Figure 2:
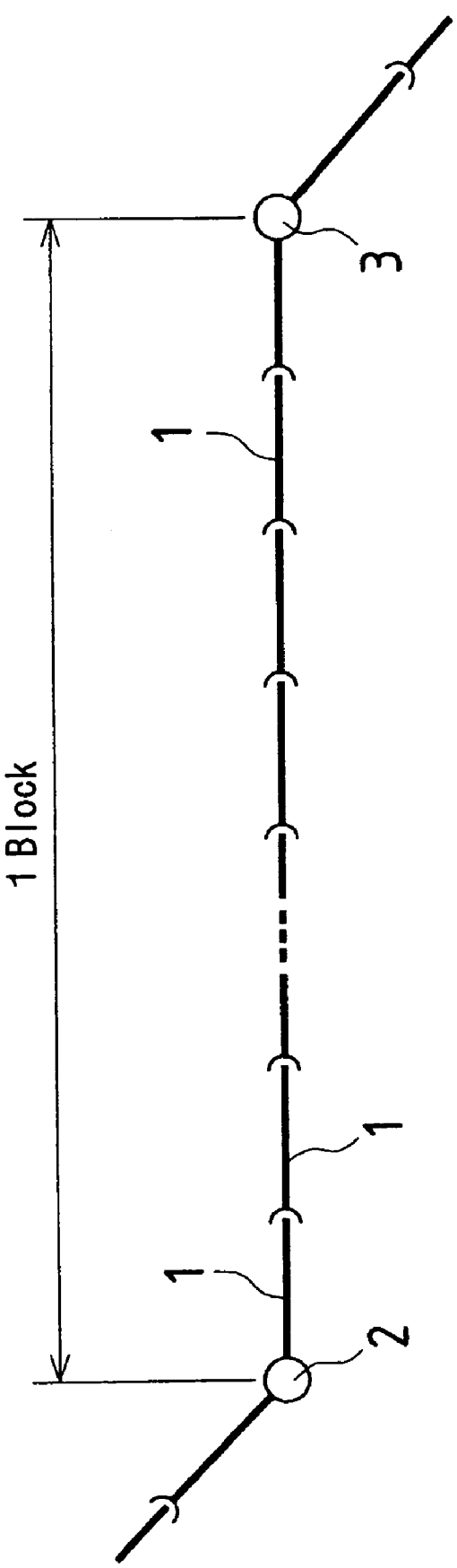
FIG. 2 is a diagram showing an example of a block to be inspected.

In this embodiment, as shown in FIG. 2, assuming that the segment from a manhole 2 to a manhole 3 is one block, tests, measurements and the like, which will be described later, are carried out on each of the reinforced concrete pipe 1 (Hume pipe) constituting the one block.

[Washing Step S0]

When a large amount of extraneous matter remains on the inner surface of the pipe to be inspected, defects are prevented from being detected. The extraneous matter is to be removed by means of cutting using a cutting machine or a water jet washing.

[Inspection step S1]

The following appearance test and impact elastic wave test are carried out.

<Appearance Test>

Corrosion abrasion, cracks, breakage, leakage of water or the like, which are recognizable on the inner surface of the pipe, are checked. As for the inspection method, when the diameter of the pipe to be inspected is large enough, an inspector carries out the inspection by the naked eye. When the diameter is too small for the inspector person (criterion: ϕ800 mm), a TV camera is placed into the pipe to carry out the inspection.

<Impact Elastic Wave Test>

Hammering is carried out on the inner surface at an end portion of the pipe to be inspected using a hammer, a steel ball or an impulse hammer. Propagated waves are detected with an acceleration sensor or a microphone placed on the inner surface at the other end portion of the pipe to be inspected. Speed, decay time, magnitude, resonant frequency, phase and the like of the propagated waves are calculated and compared with a perfectly sound item to check for existing deterioration.

To detect the level of deterioration, a simple method, in which the level of deterioration is detected based on changes in the resonant frequency or changes in decay time, is available. That is, when the deterioration progresses, since the resonant frequency and the decay time decrease, the deterioration level can be readily detected in a quantitative manner.

In the impact elastic wave test, it is preferred to apply the hammering with the same force on a constant basis. For example, a method, in which a steel ball or the like is released using a Schmitt hammer or a spring; or, a method, in which a steel ball or the like is dropped from a specific height, is employed. Further, a method, in which hammering force of an impulse hammer is measured beforehand in order to take into consideration the influence of the hammering force at data analysis, may be employed.

In the inspection in step S1, the impact elastic wave test may be carried out only in an area other than the area where it can be determined as obviously being deteriorated by the appearance test. In order to correctly classify the progression level of the deterioration, both tests of the appearance test by visual check (TV camera) and the impact elastic wave test may be carried out in the entire area. That is, by carrying out the impact elastic wave test, based on the test result, the progression level of deterioration in the component segment constituting area to be inspected can be classified.

In the inspection in step S1, when it is determined that the inspected pipe is difficult to be used, the following steps S2 to S7 may be omitted. And the reinforced concrete pipe may be replaced with a new one immediately.

[Inspection Portion Selecting Step S2]

Portion to be inspected in detail is selected based on the inspection result of the inspection in step S1.

The criterion of the selection from the following criteria may be employed; i.e., (1) a portion where the deterioration has most progressed; (2) a portion where the progress level of the deterioration is intermediate; (3) a portion where no deterioration is found; and (4) a combination of (1) and (2) above. However, from the point of view of preventing an accident from occurring during actual use, it is preferred to select "a portion where the deterioration has most progressed."

[Measuring Step S3]

Measurement of pipe thickness to be inspected, determination of deteriorated portion (position of cracks) and measurement of depth of cracks are carried out. In any measurements, elastic waves of 20 kHz to 1 MHz are injected from an injecting device into the pipe to be inspected, and the propagated waves are detected and measured by a receiving unit. When the frequency of the elastic wave is 20 kHz or less, quantitative measurement is impossible; and when it is higher than 1 MHz, a large diffusion results and the analysis is difficult.

As for the injecting device, a transmitter (vibrator) employing a piezoelectric element is preferably used. Also, as for the receiving unit, a receiver employing a piezoelectric element is preferably used.

Each item for measurement will be described.

<Measurement of Pipe Thickness>

Based on the propagation time from a point in time when elastic waves are injected into the wall of the pipe from the inside of the pipe to be inspected up to a point in time when the elastic waves, which are reflected at the outer surface of the pipe, are detected by the receiving unit, the pipe thickness is measured. For measurement of thickness of pipe, for convenience of measurement, a transmitting/receiving sensor, in which a transmitter and a receiver are integrated, is preferably used.

<Determination of Deteriorated Portion>

Receivers are disposed at a plurality of points on the pipe to be inspected, and the propagation time from the transmitter to each receiver is measured to determine deteriorated portions.

<Measurement of Crack Depth>

The depth of cracks in the determined deteriorated portion is measured using, for example, a method set forth in "Concrete Diagnosis Technique 1) 1 [Basic] 4.4.2 (5) (a) (c);" or a technique disclosed in Japanese Published Examined Patent Application No. H6-52259.

It is not always necessary to carry out the above measurement of pipe thickness, determination of the deteriorated portion and measurement of the depth of cracks. Depending on the deterioration state, the items may be appropriately selected.

For example, when it is apparent that the deterioration is abrasion only, only the measurement of pipe thickness is carried out. When the deterioration is a crack only, only the determination of the deteriorated portion and the measurement of the depth of a crack is carried out.

[Reinforcing Bar Disposition Checking Step S4]

The disposition of reinforcing bars is checked using an electromagnetic induction type inspection machine or an electromagnetic wave type inspection machine, which are generally available from the market. As inspection machines of this type, an X-ray type is also available. However, in the case of the X-ray type, since the pipe wall has to be transmitted, it is difficult to apply the X-ray type inspection machine to the existing concrete pipes.

When the disposition of the reinforcing bars is recorded in drawings or the like, the disposition of reinforcing bars in the drawings may be used as the data, and the checking step of the disposition of reinforcing bars using an inspection machine may be omitted accordingly.

[Concrete Solid-State Properties Measuring Step S5]

Strength of concrete is measured by means of a compressive strength test using a common core sampling, a needle insertion test (Japanese Published Unexamined Patent Application No. H10-090150) using a small diameter core or a strength test using a Schmitt hammer and the like.

When the strength of concrete is measured by means of core sampling, the progression level of neutralization of the reinforcing bars may be measured using an indicator such as phenolphthalein.

[Reinforcing Bar Diameter Measuring Step S6]

Core sampling is carried out, and when a reinforcing bar is included, the diameter of the reinforcing bar is measured directly.

Further, as another method, the following method may be employed. That is, a part of the concrete is broken off, Using a self-potential method for detecting the corrosion level of the reinforcing bar based on the potential difference between the exposed reinforcing bar and the surface of the concrete, the relationship between the reinforcing bar corrosion level and the diameter of the reinforcing bar is calculated beforehand. The diameter of the reinforcing bar is calculated based on the corrosion level of an object. When breaking off, using an indicator such as phenolphthalein, the progression level of neutralization of the reinforcing bar may be measured.

Here, in the above described measuring step S3, when the reinforcing bars are surveyed by means of electromagnetic induction, since the diameter of the reinforcing bars can be measured at the same time, the diameter reinforcing bar measuring step S6 may be omitted.

Depending on the workability, the order of the above steps S3 to S6 may be changed.

[Calculating Step S7]

Using the data obtained in the above-described steps, structural analysis is carried out to calculate the strength of a pipe (breaking load) of the reinforced concrete pipe.

The technique of structural analysis will be described in particular.

Figure 3:
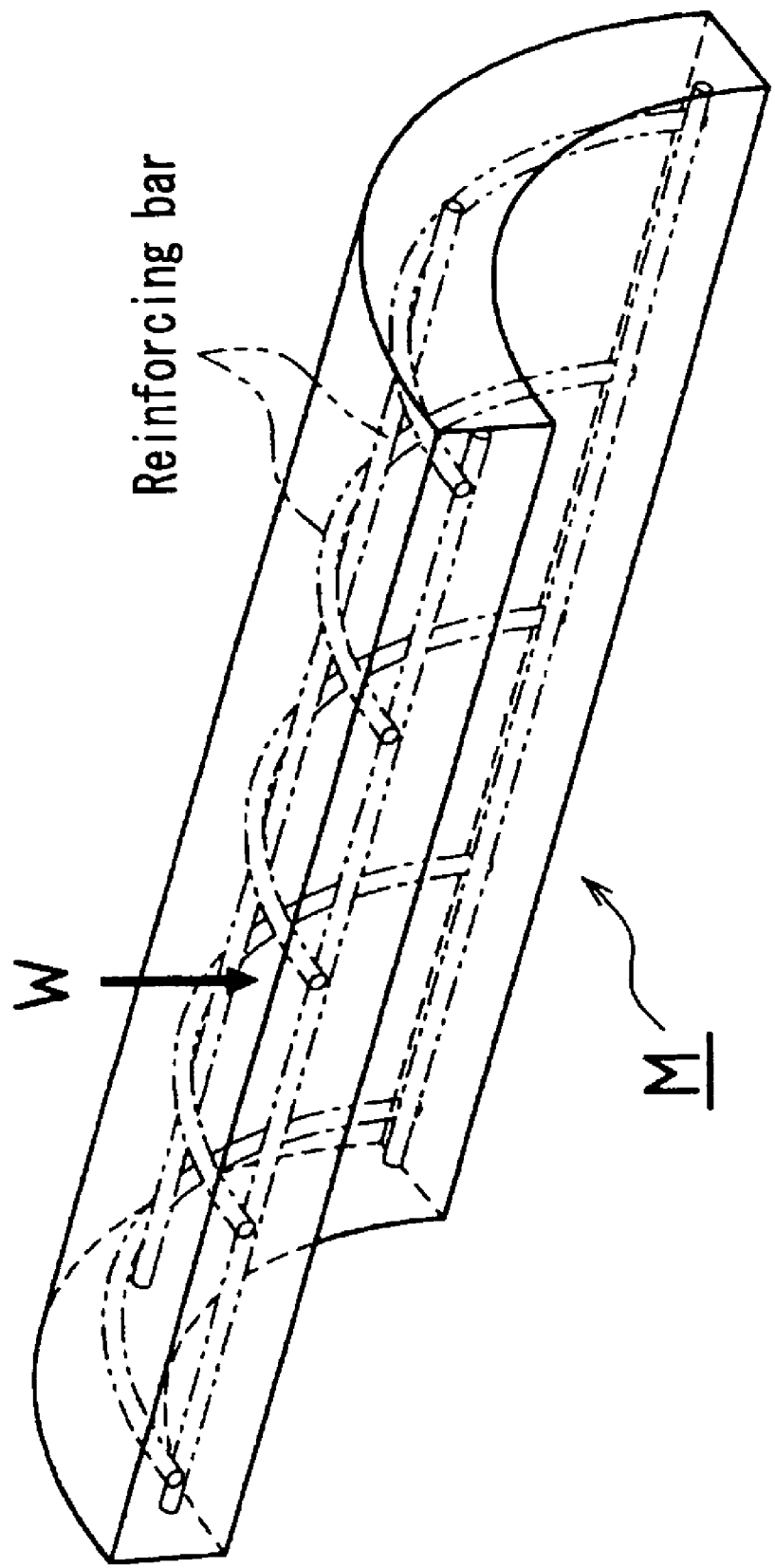
FIG. 3 is a perspective view showing a structural analysis model used in the embodiment of the present invention.
Figure 4:
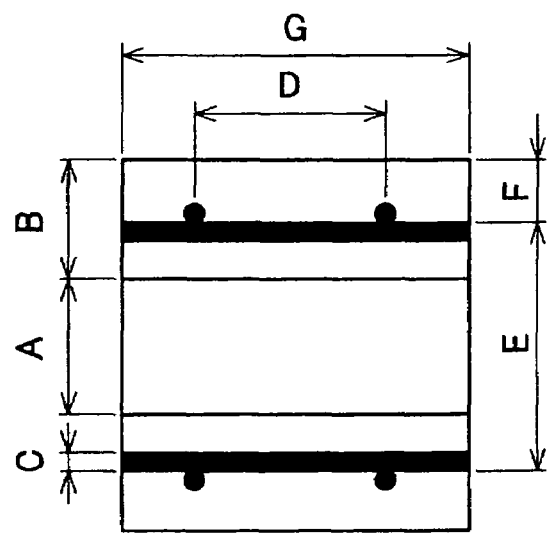
FIG. 4 is a diagram showing a configuration data used for structural analysis.

First, in a model M (¼ model) as shown in FIG. 3, configuration data as shown in FIG. 4 (A: nominal diameter, B: thickness of pipe, C: diameter of the reinforcing bar (straight reinforcing bar), D: pitch of reinforcing bar, E: cage diameter of reinforcing bar, F: depth to reinforcing bar, G: length of pipe) are given. Then, load W is applied to the center on the top of the model M. The stress in the load applying process is calculated by means calculation.

Figure 5:
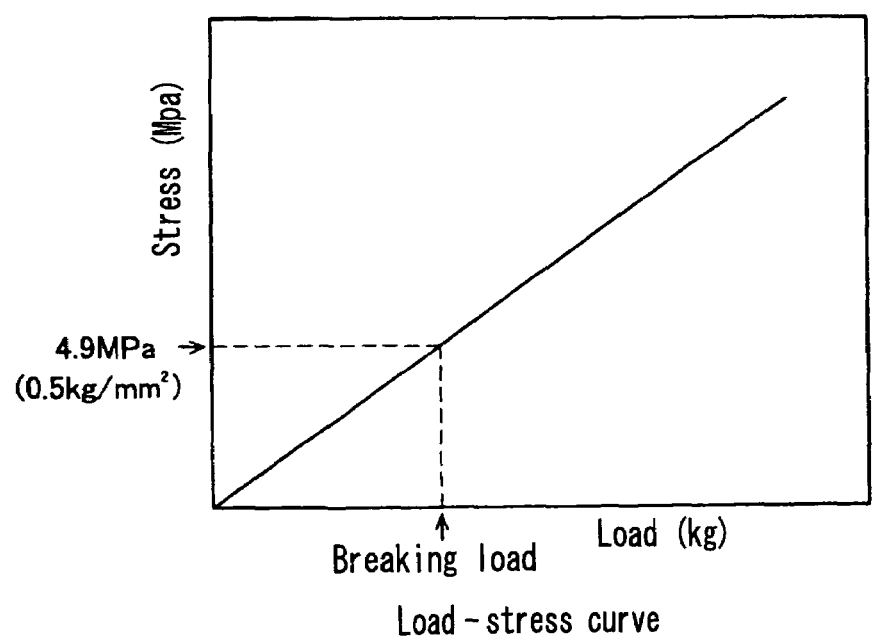
FIG. 5 is a diagram showing a load-stress curve created in the structural analysis.

Using a stress value obtained by the calculation and the load, a load-stress curve as shown in FIG. 5 is created. In the created load-stress curve, reading the breaking criterion of the concrete as 4.9 MPa (0.5 kg/mm$^2$), the breaking load was obtained.

The above-described structural analysis is carried out on the pipe to be inspected (reinforced concrete pipe) to obtain the breaking load. In the data used for structural analysis, for the thickness of pipe (B), the data, which are measured in measuring step S3, are used; and for the diameter of the reinforcing bar (straight reinforcing bar) (C), the data, which are measured in diameter reinforcing bar measuring step S6, are used. Also, for the pitch of reinforcing bar (D), the cage diameter of reinforcing bar (E) and the depth to reinforcing bar (F), the data, which are calculated based on the disposition of the reinforcing bars checked in reinforcing bar disposition checking step S4, are used.

Using the breaking load of the pipe to be inspected, which was obtained by the above-described structural analysis and calculation, and by obtaining the scale of the breaking load with respect to the designed load, the deterioration state of the pipe to be inspected can be evaluated in a quantitative manner.

In this embodiment, in the inspection step S1, the classification of the deterioration level is evaluated in a quantitative manner. Accordingly, based on the strength of the pipe in a portion to be inspected in detail, the strength of the pipe in each of the component segments can be can be estimated.

Structural calculation software for carrying out the above-described structural analysis is available on the market. It is preferable to use software to carry out the above steps efficiently.

In addition to the above-described evaluation using the breaking load, using the measurement data of the position of cracks, depth of the cracks and strength of the concrete, the deterioration state of the pipe to be inspected may be determined comprehensively.

EXAMPLE 1

A specific example of the present invention will be described.

[Preparation of Sample]

The following samples of a product (inside diameter 400 mm) manufactured by Nippon Hume Corporation conforming to JIS A 5303 Type A-2 was prepared.

Sample T11: perfectly sound product

Sample T12: item introduced with water leak crack (deterioration progress level maximum)

Figure 6:
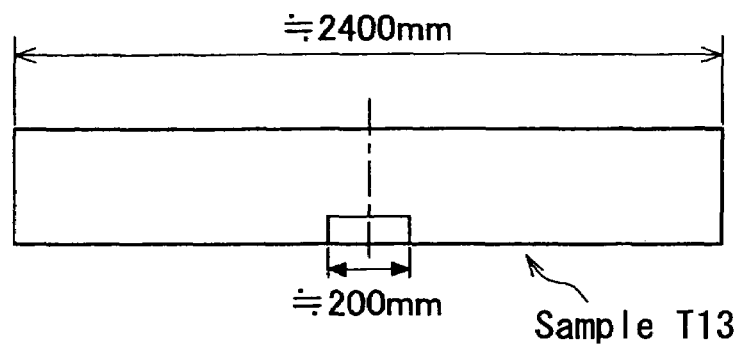
FIG. 6 is a diagram for illustrating a sample T13 used in an example of the present invention.

Sample T13: item of which a part (central area) of bottom portion in the pipe inner surface was corroded with 1% vitriolic acid by approximately 1 mm in thickness (refer to FIG. 6)

[Measuring Device]

Hammer: Schmitt hammer NR (manufactured by Fuji Bussan Co., Ltd.)

Receiver: AS-5 GB (manufactured by KYOWA Instruments Co., Ltd.)

Recording unit: EDX1500A (with amplifier) (manufactured by KYOWA Instruments Co., Ltd.)

[Disposition of Measuring Device]

Figure 7:
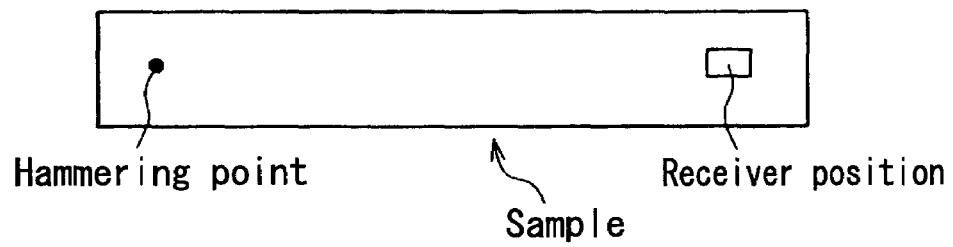
FIG. 7 is a diagram showing a location of a measuring device on a sample.

Disposition shown in FIG. 7 was employed.

[Analysis Resonant Frequency]

The data of the propagated elastic wave, which were measured using the disposition of the measuring devices shown in FIG. 7, were processed into a power spectrum of the resonant frequency using an FFT function provided for the recording unit to obtain the top peak. The results are shown in Table 1.

By carrying out the above process, classification of the deterioration of the reinforced concrete pipe can be determined quantitatively.

Embodiment 2

Another embodiment of the present invention will be described.

An injecting device and receiver used in the impact elastic wave test will be described first.

As for the injecting device, a hammering tool such as a hammer, a steel ball or an impulse hammer is available. In the impact elastic wave test, since it is preferred to carry out the hammering with the same force on a constant basis, for example, a method, in which the steel ball or the like is released with a specific force using a Schmitt hammer or spring; or a method, in which the steel ball or the like is dropped from a specific height, is employed. Further, a method, in which the hammering force of the impulse hammer is measured beforehand to take the influence of the hammering force into consideration during the data analysis, may be employed.

As for the receiver, an acceleration sensor, an AE sensor and vibration sensor or the like is available.

As for the setting method of the receiver, the receiver may be fixed using an adhesive tape or agent, or may be brought into contact with the object by hand, a holding tool or the like.

The injecting device and receiver may come into contact with water, acid water or basic water. Accordingly, the injecting device and receiver are preferably constituted with a material such as SUS, which is superior in anti-corrosion.

Next, the measuring method and analyzing method of the received waves will be described.

[Measuring Method]

An impact is given to the inner surface at an end portion of a pipe to be inspected using the injecting device, the propagated waves are detected by the receiver, which is set on the inner surface at other end portion of the pipe to be inspected, and the waveform data is stored in the recording unit. In the measurement described above, it is preferred that the distance between the elastic wave injecting position by the injecting device and the elastic wave receiving position by the receiver is ¼ or more of the length of the pipe to be inspected away from each other. By prescribing the distance between the elastic wave injecting position and the elastic wave receiving position as described above, the changes in vibration mode of the entire pipe due to deterioration caused from cracks can be detected easily.

[Analyzing Method of the Received Waves]

Figure 11:
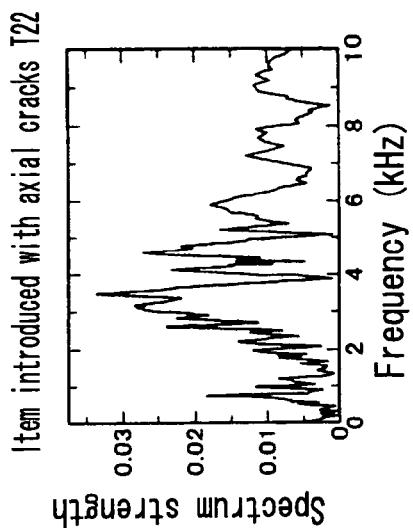
FIG. 11 are spectrum charts of resonant frequency of each sample.
Figure 11:
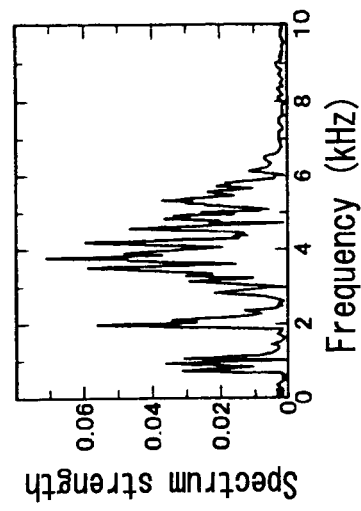
Figure 11:
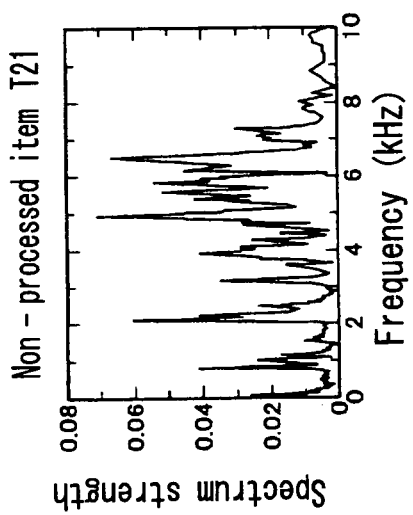
Figure 11:
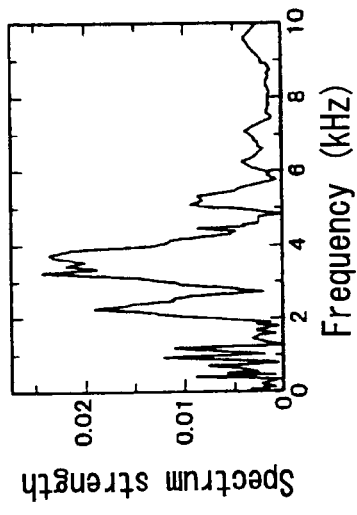

First, FFT analysis is made on the waveform data stored in the recording unit, and a resonant frequency spectrum chart is created (refer to FIG. 11). Then, integration processing is made on the created resonant frequency spectrum chart, and a high frequency component and low frequency component are obtained. And thus, the area ratio between the area of the high frequency component and the area of the low frequency component is calculated. In particular, with respect to the resonant frequency spectrum, by dividing with 4 kHz as the boundary, area ratios between the range of 0 to 4 kHz and the range of 4 to 8 kHz are obtained, and the deterioration level of the pipe to be inspected is determined based on the area ratio.

In the above analysis, the boundary value (for example 4 kHz) between the high frequency and the low frequency may be preset. It is preferred to make a determination at the measuring site depending on the type of the pipe to be inspected for facilitating the determination.

EXAMPLE 2

A specific example of the present invention will be described.

[Sample Preparation]

Figure 8:
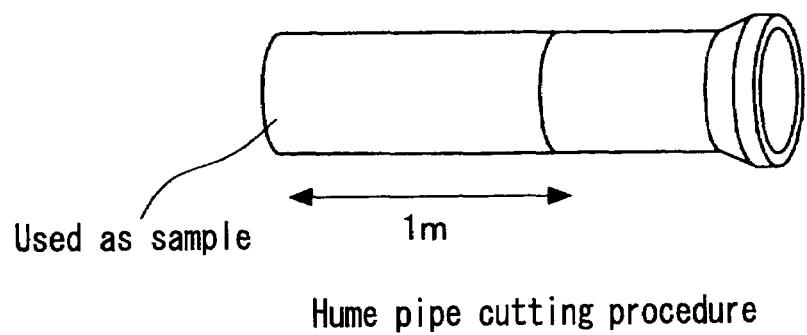
FIG. 8 is a diagram schematically showing a preparation step of a sample used in an example of the present invention.

The following samples were prepared using a product (inside diameter 250 mm) manufactured by Nippon Hume Corporation, conforming to JIS A 5303 type B, which were cut off as shown in FIG. 8

Sample T21: Unprocessed product

Sample T22: item introduced with axial cracks

Dropped on concrete surface to generate four cracks in the axial direction

Sample T23: item introduced with axial cracks

Figure 10:
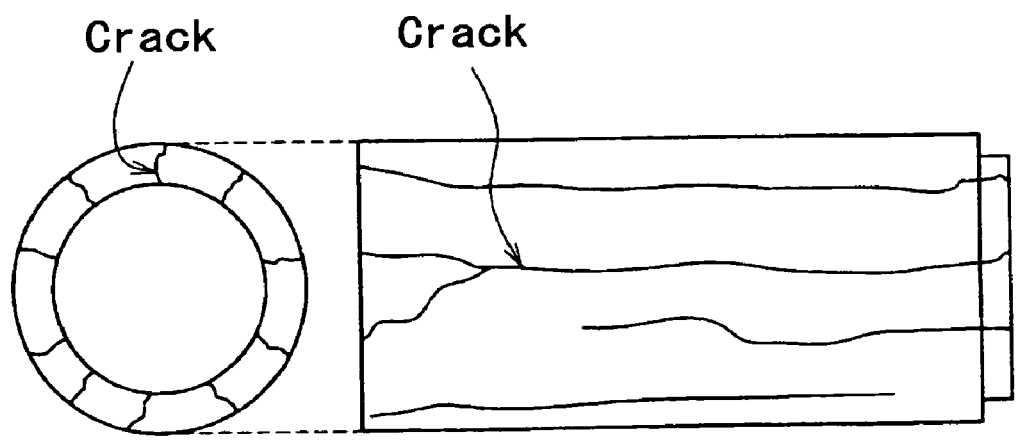
FIG. 10 is an illustration schematically showing a sample introduced with axial cracks.

Dropped on concrete surface to generate ten cracks in the axial direction (refer to FIG. 10). As for the number of the cracks in the samples T22 and T23, the number of cracks generated on the inner and outer surfaces was checked at one end surface by visual check.

Sample T24: item of which inner surface was ground.

The reinforcing bars were exposed out of the inner surface layer by means of water jet blasting. Amount of grinding was set so as to be 1.6 mm in average grinding thickness. The ground amount was measured at ten points on each end in an area adjacent to the pipe end; total 20 points, using a slide caliper.

List of samples is shown in Table 2.

[Injection and Receiving Position]

Figure 9:
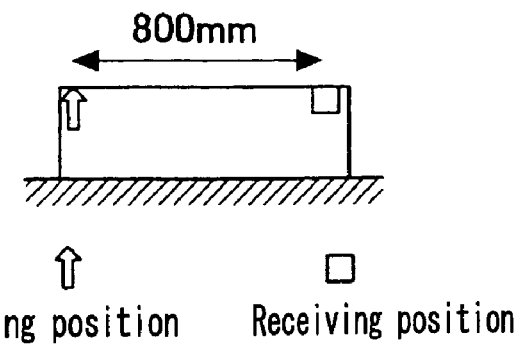
FIG. 9 is a diagram showing a location of measuring devices on a sample.

The injecting device and the receiving unit are disposed at the positions shown in FIG. 9, and injection of elastic waves and reception of propagation waves were performed.

[Used Apparatus]

Injecting device: P type Schmitt hammer

Receiver: a cylindrical item of a diameter of 1 mm and height of 15 mm, was attached onto a male screw on a vibration sensor GH-313A (manufactured by Keyence Corporation). The receiver was set and held by hand.

Receiving amplifier: GA-245 (manufactured by Keyence Corporation)

Data logger (recording unit): NR-350 (manufactured by Keyence Corporation)

[Data Analysis]

Using the waveform data of the propagation waves received and recorded with the above apparatus, power spectrum of the resonant frequency was created by using the FFT analyzing program (manufactured by APTEC). Resonant frequency spectrums of the respective samples are shown in FIGS. 11(a) to (d).

Figure 12:
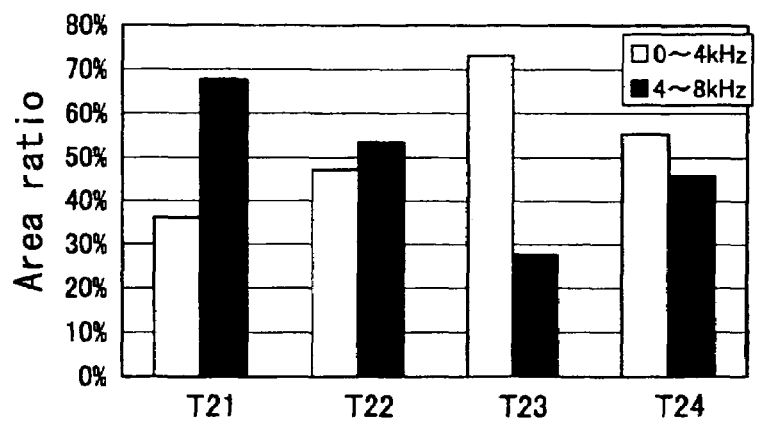
FIG. 12 is a graph showing the frequency component ratio of each sample.

Then, with respect to each of the resonant frequency spectrums in FIGS. 11(a) to (d), by dividing with 4 kHz as the boundary, area ratios between the range of 0 to 4 kHz and the range of 4 to 8 kHz are obtained by Igor Pro (manufactured by Wave Metrics) The results are shown in Table 3 and FIG. 12.

As demonstrated in Table 3 and FIG. 12, it is understood that, when the progression level of the deterioration becomes large, the ratio of the low frequency component becomes higher. Accordingly, based on the area ratio between the high frequency component and the low frequency component in the resonant frequency spectrum of the propagation waves, the deterioration level of the pipe to be inspected can be determined quantitatively.

Embodiment 3

Another embodiment of the present invention will be described.

First, the injecting device and receiver used for the impact elastic wave test will be described.

As for the injecting device, a hammering tool such as a hammer, a steel ball or an impulse hammer is available. In the impact elastic wave test, since it is preferred to carry out the hammering with the same force on a constant basis, for example, a method, in which the steel ball or the like is released with a specific force using a Schmitt hammer or spring, or a method, in which the steel ball or the like is dropped from a specific height, is employed. Further, a method, in which the hammering force of the impulse hammer is measured beforehand to take the influence of the hammering force into consideration during the data analysis, may be employed.

As for the receiver, an acceleration sensor, an AE sensor and vibration sensor or the like is available.

As for the setting method of the receiver, the receiver may be fixed using an adhesive tape or agent, or may be brought into contact with the object by hand, a holding tool or the like.

The injecting device and receiver may come into contact with water, acid water or basic water. Accordingly, the injecting device and receiver are preferably constituted of a material such as SUS, which is superior in anti-corrosion.

Next, the measuring method and analyzing method of the received waves will be described.

[Measuring Method]

An impact is given to the inner surface at the end portion of a pipe to be inspected using the injecting device, the propagated waves are detected by the receiver set on the inner surface at the other end portion of the pipe to be inspected, and the waveform data is stored in the recording unit. In the measurement described above, it is preferred that the distance between the elastic wave injecting position by the injecting device and the elastic wave receiving position by the receiver is ¼ or more of the length of the pipe to be inspected away from each other. By prescribing the distance between the elastic wave injecting position and the elastic wave receiving position as described above, the changes in vibration mode of the entire pipe due to deterioration caused from cracks can be detected easily.

[Analyzing Method of Received Wave]

Figure 15:
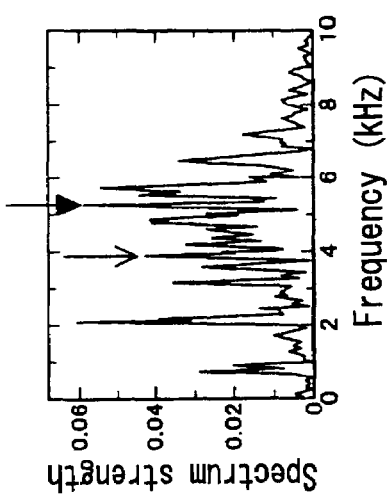
FIG. 15 are resonant frequency spectrum charts of each sample.
Figure 15:
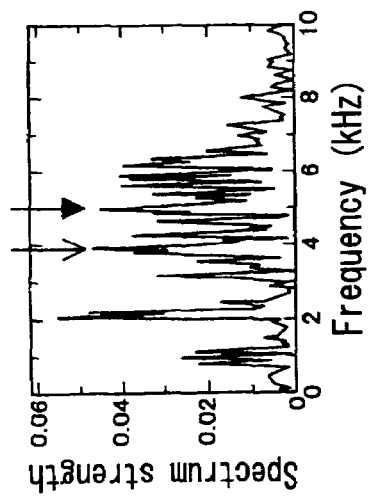
Figure 15:
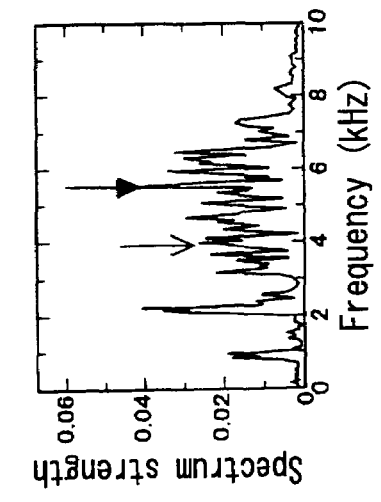

First, FFT analysis is made on the waveform data stored in the recording unit, and a resonant frequency spectrum chart is created (refer to FIG. 15). Then, the strength ratio between the top peak strength in the frequency range of 4 to 10 kHz (high frequency range) and the top peak strength in the frequency range of 3 to 4 kHz (low frequency range) of the created resonant frequency spectrum is calculated. And based on the calculated top peak strength ratio, the deterioration level of the pipe to be inspected is determined.

In this embodiment, a phenomenon, in which, as the deterioration of the reinforced concrete pipe proceeds, the vibration mode changes, and the vibration constituting the resonant frequency also changes, is utilized.

EXAMPLE 3

A specific example of the present invention will be described.

[Sample Preparation]

The following samples were prepared using a product (inside diameter 250 mm) manufactured by Nippon Hume Corporation, conforming to JIS A 5303 type B, which were cut off as shown in FIG. 8

Sample T31: Non-processed

Sample T32: Item introduced with peripheral cracks

Figure 13:
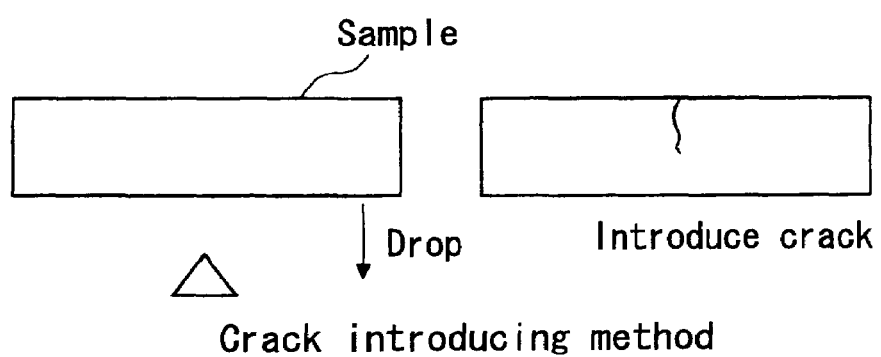
FIG. 13 is a diagram schematically showing a crack introducing method employed in an example of the present invention.
Figure 14:
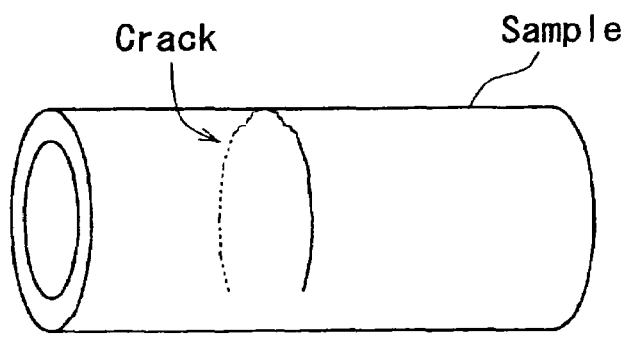
FIG. 14 is an illustration schematically showing a sample introduced with a peripheral crack.

Item, which is introduced with a crack of 0.15 mm in width by means of introduction as shown in FIG. 13 (refer to FIG. 14).

Sample T33: Item introduced with peripheral cracks

Item, which is introduced with a crack of 1.3 mm in width by means of introduction as shown in FIG. 13 (refer to FIG. 14). The width of cracks in the samples T32 and T33 were measured while being enlarged by a magnifier with a scale (average of values at 5 points).

List of samples is shown in Table 4.

[Injection and Receiving Position]

The injecting device and the receiving unit were disposed at the position shown in FIG. 9, and the injection of elastic waves and reception of the propagated waves were carried out.

[Used Apparatus]

Injecting device: P type Schmitt hammer

Receiver: a cylindrical item of a diameter of 10 mm, a height of 15 mm, was attached onto a male screw on a vibration sensor GH-313A (manufactured by Keyence Corporation). The receiver was set and held by hand.

Receiving amplifier: GA-245 (manufactured by Keyence Corporation)

Data logger (recording unit): NR-350 (manufactured by Keyence Corporation)

[Data Analysis]

Using the waveform data of the propagation waves received and recorded with the above apparatus, power spectrum of the resonant frequency was created by using the FFT analyzing program (manufactured by APTEC). Resonant frequency spectrums of the respective samples are shown in FIGS. 15(*a*) to (*c*).

Then, with respect to each of the resonant frequency spectrums in FIGS. 15(*a*) to (*c*), the top peak strength in the frequency range (high frequency range) of 4 to 10 kHz and the top peak strength in the frequency range (low frequency range) of 3 to 4 kHz were calculated. And the strength ratio between the top peak strength in the frequency range of 4 to 10 kHz and the top peak strength in the frequency range of 3 to 4 kHz was calculated. The results are in Table 5.

As demonstrated in Table 5, when the progression level of deterioration of the pipe to be inspected becomes larger, the ratio (P1/P2) of the top peak strength (P1) in the frequency range of 4 to 10 kHz with respect to the top peak strength (P2) in the frequency range in 3 to 4 kHz becomes larger. Accordingly, by obtaining the ratio between the top peak strength in the frequency range of 4 to 10 kHz and the top peak strength in the frequency range of 3 to 4 kHz in the resonant frequency spectrum of the propagation waves, based on the strength ratio, the deterioration level of the pipe to be inspected can be determined quantitatively.

Embodiment 4

Still another embodiment of the present invention will be described.

Injecting device and receiver used in the impact elastic wave test will be described first.

As for the injecting device, a hammering tool such as a hammer, a steel ball or an impulse hammer is available. In the impact elastic wave test, since it is preferred to carry out the hammering with the same force on a constant basis, for example, a method, in which the steel ball or the like is released with a specific force using a Schmitt hammer or a spring, or a method, in which the steel ball or the like is dropped from a specific height is employed. Further, a method, in which hammering force of the impulse hammer is measured beforehand to take the influence of the hammering force into consideration during the data analysis, may be employed.

As for the receiver, an acceleration sensor, an AE sensor and vibration sensor or the like is available.

As for the setting method of the receiver, the receiver may be fixed using an adhesive tape or agent, or may be brought into contact with the object by hand, a holding tool or the like.

The injecting device and receiver may come into contact with water, acid water or basic water. Accordingly, the injecting device and receiver are preferably constituted of a material such as SUS, which is superior in anti-corrosion.

Next, the measuring method and analyzing method of the received waves will be described.

[Measuring Method]

An impact is given to the inner surface at the end portion of a pipe to be inspected using the injecting device, the propagated waves are detected by the receiver set on the inner surface at the other end portion of the pipe to be inspected, and the waveform data is stored in the recording unit. In the measurement described above, it is preferred that the distance between the elastic wave injecting position by the injecting device and the elastic wave receiving position by the receiver is ¼ or more of the length of the pipe to be inspected away from each other. By prescribing the distance between the elastic wave injecting position and the elastic wave receiving position as described above, the changes in vibration mode of the entire pipe due to deterioration caused from cracks can be detected easily.

[Analyzing Method of the Received Waves]

Figure 16:
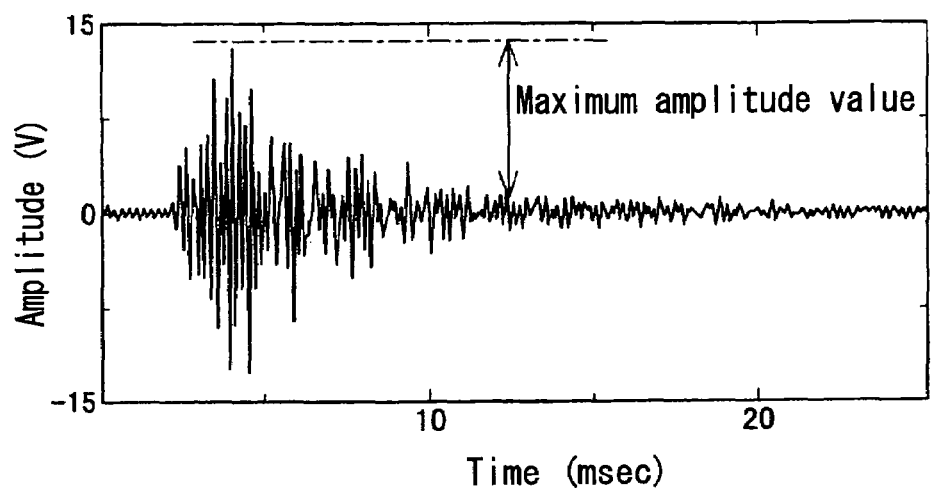
FIG. 16 is a diagram for illustrating a maximum amplitude value of a propagation wave.

First, the maximum amplitude value in the propagation waves stored in the recording unit was obtained, based on maximum magnitude value, the deterioration level of the entire pipe to be inspected is determined. The "maximum amplitude value of the propagation wave" is defined as a maximum amplitude value at which the absolute value is the maximum in the waveform data of the propagation waves as shown in FIG. 16.

EXAMPLE 4

A specific example of the present invention will be described.

[Sample Preparation]

The following samples were prepared using a product (inside diameter 250 mm) manufactured by Nippon Hume Corporation, conforming to JIS A 5303 type B, which were cut off as shown in FIG. 8.

Sample T41: non-processed item

Sample T42: item introduced with axial cracks

Item dropped on a concrete surface and generated with four cracks in the axial direction.

Sample T43: item introduced with axial cracks

Item dropped on concrete surface and generated with ten cracks in the axial direction (refer to FIG. 10). The number of the cracks in the samples T42 and T43, which were generated on the inner and outer surface, was visually checked at one end surface thereof.

Sample T44: item introduced with peripheral cracks

Item generated with cracks with width of 0.15 mm in the peripheral direction by means of crack introducing method shown in FIG. 13 (refer to FIG. 14).

Sample T45: item introduced with peripheral cracks

Item generated with cracks with width of 1.3 mm in the peripheral direction by means of crack introducing method shown in FIG. 13 (refer to FIG. 14). The width of cracks in the samples T44 and T45 were measured while being enlarged by a magnifier with a scale (average of values at 5 points).

The list of samples is shown in Table 6.

[Injection and Receiving Position]

The injecting device and the receiving unit are disposed at positions shown in FIG. 9, injection of elastic waves and reception of propagation waves were carried out.

[Used Apparatus]

Injecting device: P type Schmitt hammer

Receiver: a cylindrical item of a diameter of 10 mm, a height of 15 mm, was attached onto a male screw on a vibration sensor GH-313A (manufactured by Keyence Corporation). The receiver was set and held by hand.

Receiving amplifier: GA-245 (manufactured by Keyence Corporation)

Data logger (recording unit): NR-350 (manufactured by Keyence Corporation)

[Data Analysis]

Using the waveform data of the propagation waves received and recorded with the above apparatus, maximum amplitude values (refer to FIG. 16) of the samples were obtained. The results are shown in Table 7.

As demonstrated in Table 7, when the deterioration progression level of the pipe to be inspected becomes larger, the maximum amplitude value of the propagation waves becomes smaller. Accordingly, by obtaining the maximum amplitude value of the propagation waves from the waveform data, based on the maximum amplitude value, the deterioration level of the pipe to be inspected can be determined quantitatively.

Embodiment 5

In this embodiment, from the data indicating the deterioration phenomena; i.e., (1) the area ratio between the high frequency component and the low frequency component in a resonant frequency spectrum of the propagation waves; (2) the ratio of the top peak strength between the frequency range of 4 to 10 kHz and the frequency range of 3 to 4 kHz in a resonant frequency spectrum of the propagation waves; (3) maximum amplitude value of the propagation waves; and (4) a combination of data of the decay time of the propagation waves, the classification of deterioration phenomenon and deterioration progression level can be determined based on Table 8.

Figure 17:
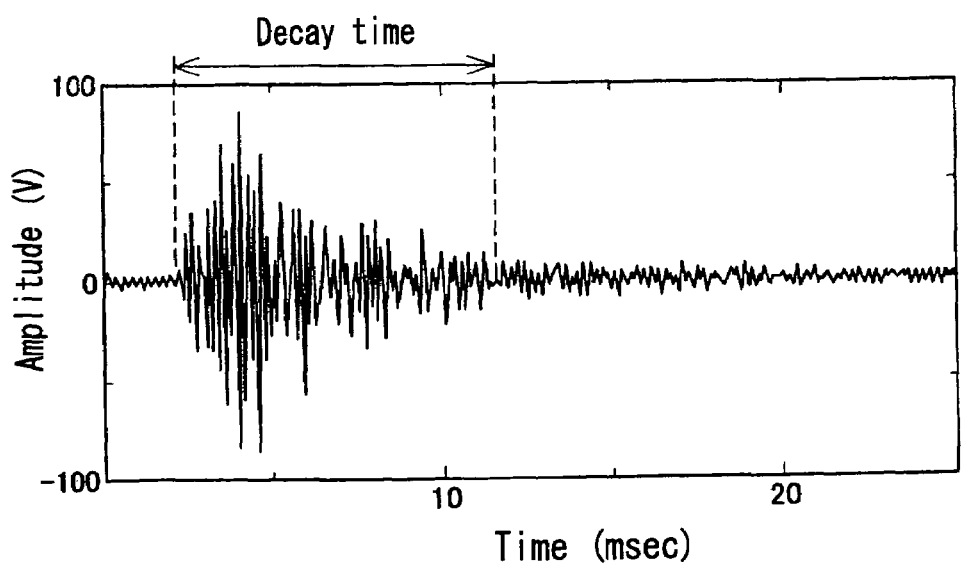
FIG. 17 is a diagram for illustrating the decay time of a propagation wave.

Here, the wording "decay time of propagation waves" means a period of time when the amplitude value of the propagation waves (received waves) becomes a certain value or less as shown in FIG. 17. In particular, for example, when vibrations, in which the absolute value of the amplitude value is 20% or less with respect to the absolute value of the maximum amplitude value, continue for three times or more, it is defined that the waves up to the first point are "input waves;" and the period of time up to the first point is "decay time."

Next, referring to the flowcharts shown in FIG. 18 to FIG. 22, an example of a particular determination processing will be described.

Figure 18:
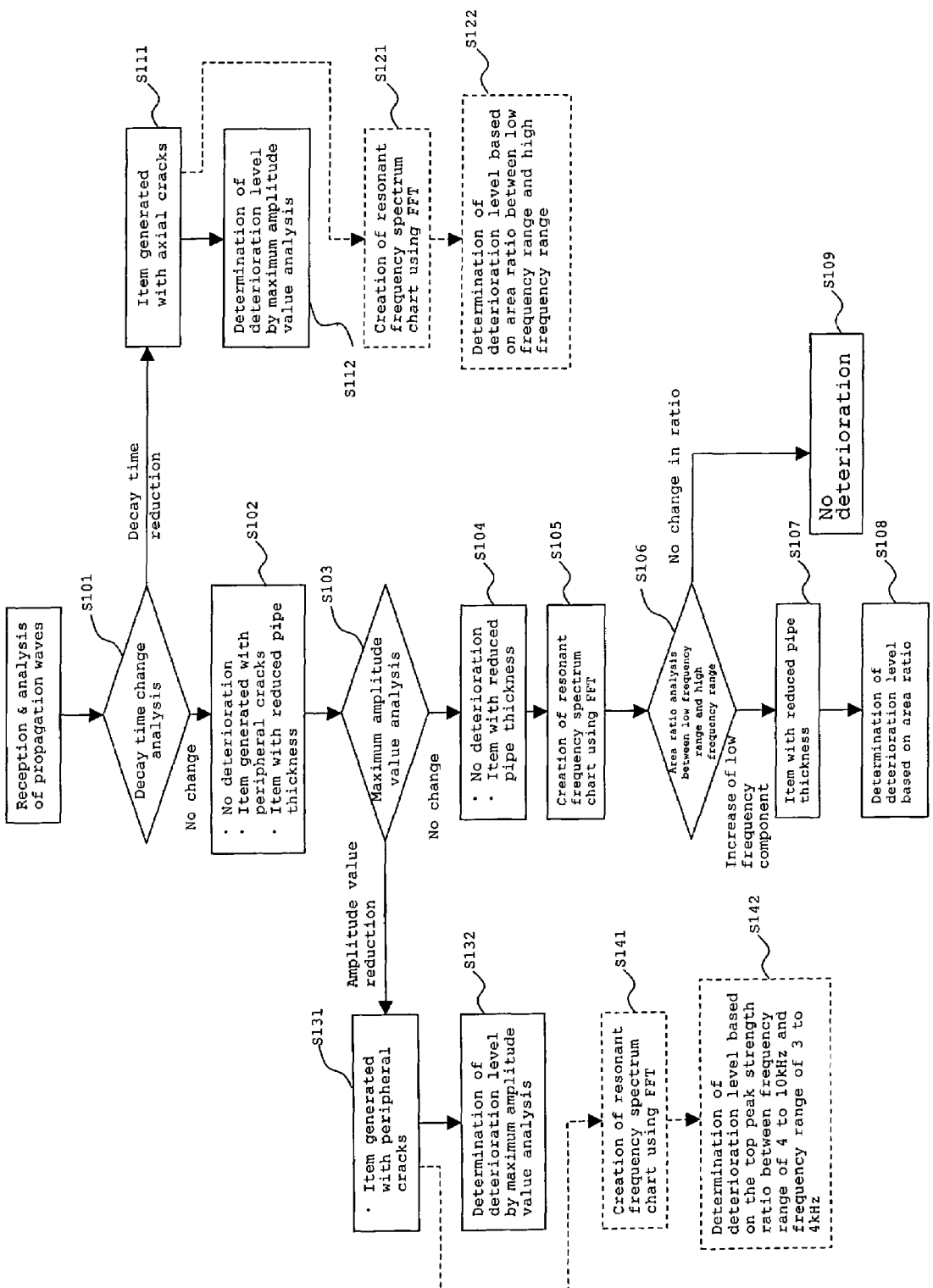
FIG. 18 is a flowchart showing the steps in determination processing, which are applied to the embodiment of the present invention.

[Determination Processing J1: FIG. 18]

Step S101: Analysis of changes in the decay time of the propagation waves. When no change is found in the decay time, the process proceeds to step S102. When a change is found in the decay time, the process proceeds to step S111. The analysis of the change in the decay time is made by comparison with a perfectly sound item.

Step S102: When no change is found in the decay time of the propagation waves, the item is recognized as "no deterioration," or, either or both of "item with peripheral crack" and/or "item with reduced pipe thickness" are possible (refer to Table 8).

Step S103: Analysis of the maximum amplitude value of the propagation waves. When no change is found in the maximum amplitude value, the process proceeds to step S104. When a change is found in the maximum amplitude value, the process proceeds to step S131. The analysis of the changes of maximum amplitude value is made by comparison with a perfectly sound item.

Step S104: When no change is found in the decay time or the maximum amplitude value of the propagation waves, the item is recognized as "no deterioration" or "item with reduced pipe thickness" (refer to Table 8).

Step S105: Resonant frequency spectrum chart (refer to FIG. 11) is created using the FFT.

Step S106: Analysis of the area ratio between the low frequency range and the high frequency range in the resonant frequency spectrum (for a detailed analysis process, refer to the above-described Embodiment 2). When a change is found in the area ratio, (increase of low frequency component), the item is determined as "item with reduced pipe thickness" (step S107). Based on the area ratio, the deterioration level is determined (step S108). On the other hand, when no change is found in the area ratio, the item is determined as "no deterioration" (step S109).

Step S111: In the analysis in step S101, when a change is found in decay time (reduction), the item is recognized as "item generated with axial crack." When the pipe to be inspected is recognized as "item generated with axial crack," determination process of the deterioration level is carried out by means of maximum magnitude value analysis (step S112). Or, a resonant frequency spectrum chart (refer to FIG. 11) is created using the process in steps S121 and S122; i.e., FFT. Then, the area ratio between the low frequency range and the high frequency range of the resonant frequency spectrum was obtained. Based on the area ratio, processing to determine the deterioration level is carried out.

Step S131: When a change is found in the amplitude value (reduction) in the analysis in step S103, the item is recognized as "item generated with peripheral crack." When the pipe to be inspected is recognized as "item generated with peripheral crack," the deterioration level is determined by means of maximum magnitude value analysis (step S132). Or, a resonant frequency spectrum chart (refer to FIG. 15) is created using the process in steps S141 and S142; i.e., FFT. Then, the top peak strength ratio between the frequency range of 4 to 10 kHz and the frequency range of 3 to 4 kHz in the resonant frequency spectrum of the propagation waves is analyzed (for a detailed analysis process, refer to Embodiment 3). Based on the strength ratio, the deterioration level is determined.

Figure 19:
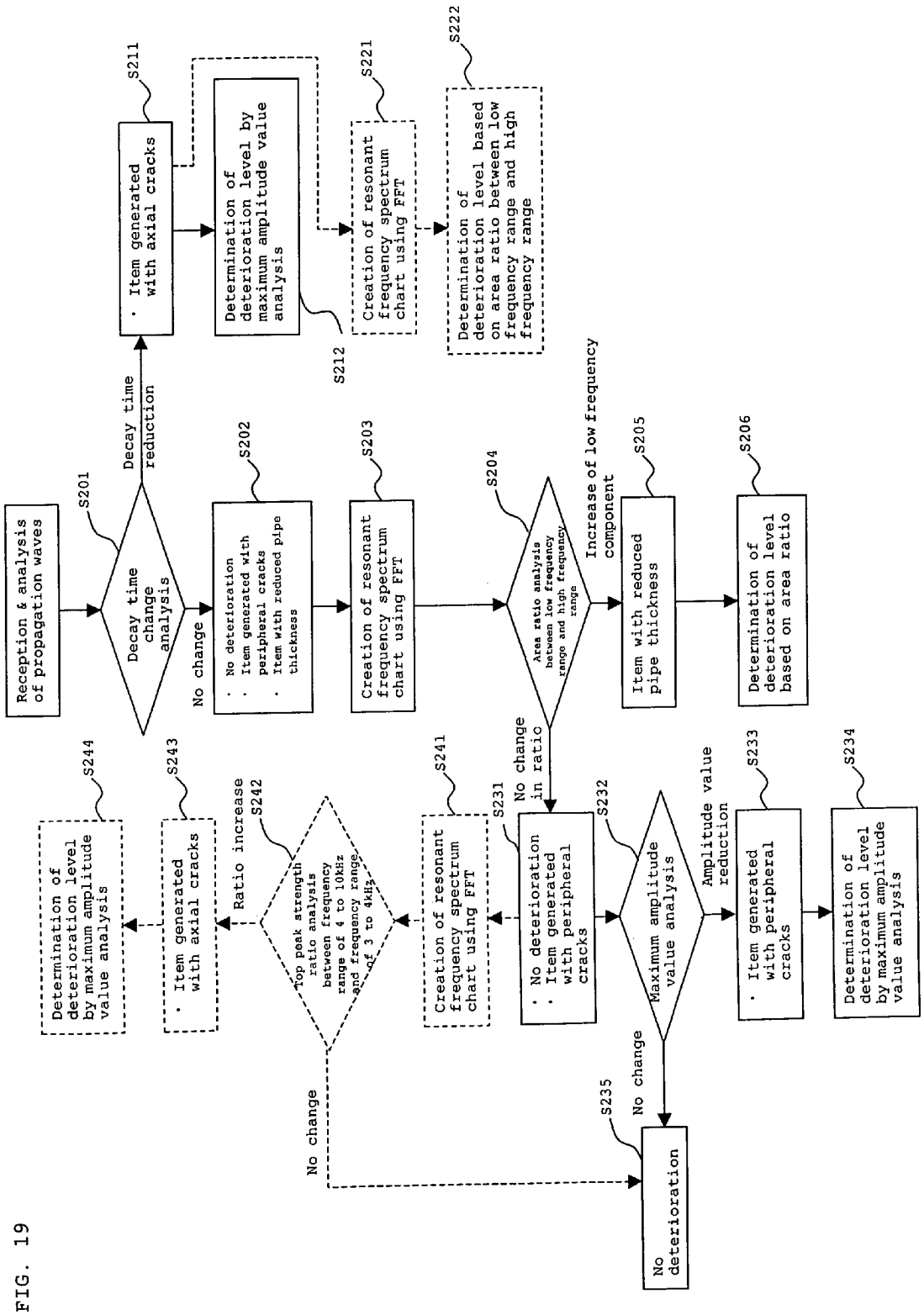
FIG. 19 is also a flowchart showing the steps in determination processing.

[Determination Processing J2: FIG. 19]

Step S201: Analysis of the changes in the decay time of the propagation waves. When no change is found in the decay time, the process proceeds to step S202. When a change is found in the decay time, the process proceeds to step S211. The analysis of changes in the decay time is made by comparison with a perfectly sound item.

Step S202: When no change is found in the decay time of the propagation waves, the item is recognized as "no deterioration," or either or both of "item generated with peripheral crack" and/or "item with reduced pipe thickness" (refer to Table 8).

Step S203: Resonant frequency spectrum chart is created using the FFT (refer to FIG. 11).

Step S204: Analysis of the area ratio between the low frequency range and the high frequency range in the resonant frequency spectrum (for a detailed analysis process, refer to Embodiment 2). When a change is found in the area ratio (increase of low frequency component), the item is determined as "item with reduced pipe thickness" (step S205). Then, based on the area ratio, the deterioration level is determined (step S206). On the other hand, when no change is found in the area ratio, the process proceeds to step S231.

Step S211: In the analysis in step S201, when a change is found in the decay time (reduction), the item is recognized as "item generated with axial crack." When the pipe to be inspected is recognized as "item generated with axial crack," the deterioration level is determined by means of maximum magnitude value analysis (step S212). Or, a resonant frequency spectrum chart (refer to FIG. 11) is created using the processing of steps S213 and S214; i.e., FFT. Then, the area ratio between the low frequency range and the high frequency range in the resonant frequency spectrum is analyzed. Based on the area ratio, processing to determine the deterioration level is carried out.

Step S231: In the analysis in step S204, when no change is found in the area ratio, the item is recognized as "no deterioration" or "item generated with peripheral crack" (refer to Table 8).

Step S232: The maximum amplitude value in the propagation waves is analyzed, and when no change is found in the maximum amplitude value, the item is recognized as "no deterioration." On the other hand, when a change is found in the maximum amplitude value (reduction in amplitude), the item is recognized as "item generated with peripheral crack" (step S233). When the pipe to be inspected is recognized as "item generated with peripheral crack," processing to determine the deterioration level is carried out (step S234) by means of maximum magnitude value analysis. Or, processing steps from S241 to S244 are carried out. The analysis of changes in the maximum amplitude value is made by comparison with a perfectly sound item.

In the processing of the steps from S241 to S244, the resonant frequency spectrum chart (refer to FIG. 15) is created using the FFT. The top peak strength ratio between the frequency range of 4 to 10 kHz and the frequency range of 3 to 4 kHz in the resonant frequency spectrum is analyzed (for a detailed analysis process, refer to the above-described Embodiment 3). In this analysis, when a change is found in the top peak strength ratio (ratio increase), the item is recognized as "item generated with peripheral crack." Then, based on the strength ratio, the deterioration level is determined. When no change is found in the top peak strength ratio in the analysis in step S242, the item is determined as "no deterioration."

Figure 20:
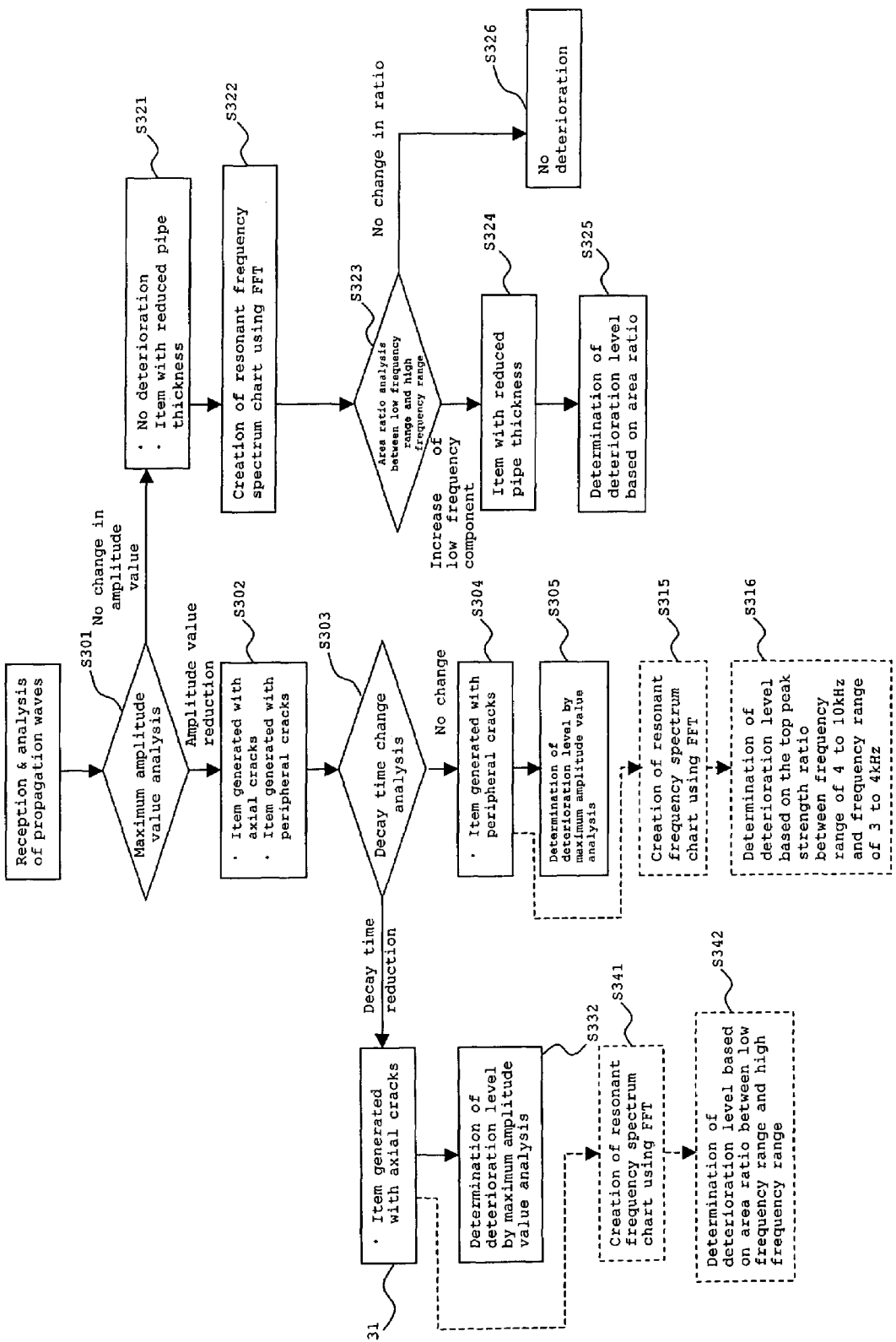
FIG. 20 is also a flowchart showing the steps in determination processing.

[Determination Processing J3: FIG. 20]

Step S301: Analysis of the maximum amplitude value of the propagation waves. When a change (reduction in amplitude) is found in the maximum amplitude value, the process proceeds to step S302. When no change is found in the maximum amplitude value, the process proceeds to step S321. The analysis of changes in the maximum amplitude value is made by comparison with a perfectly sound item.

Step S302: When a change is found in the maximum amplitude value of the propagation waves, the item is recognized as either or both of "item generated with axial crack" and/or "item generated with peripheral crack" (refer to Table 8).

Step S303: Analysis of changes in the decay time of the propagation waves. When a change is found in the decay time (reduction in decay time), the process proceeds to step S331. The analysis of changes in the decay time is made by comparison with a perfectly sound item.

On the other hand, when no change is found in the decay time, the item is recognized as "item generated with peripheral crack" (step S304). When the pipe to be inspected is recognized as "item generated with peripheral crack," the deterioration level is determined by means of maximum magnitude value analysis (step S305). Or, a resonant frequency spectrum chart (refer to FIG. 15) is created using the process in steps S315 and S316; i.e., FFT. Then, the top peak strength ratio between the frequency range of 4 to 10 kHz and the frequency range of 3 to 4 kHz in the resonant frequency spectrum of the propagation waves is analyzed (for a detailed analysis process, refer to the above Embodiment 3). Based on the strength ratio, a processing to determine the deterioration level is carried out.

Step S321: In the analysis in step S301, when no change is found in the amplitude value, the item is recognized as "no deterioration" or "item with reduced pipe thickness" (refer to Table 8).

Step S322: A resonant frequency spectrum chart is created using the FFT (refer to FIG. 11).

Step S323: The area ratio between the low frequency range and the high frequency range in the resonant frequency spectrum is analyzed (for a detailed analysis process, refer to the above Embodiment 2). When a change (increase of low frequency component) is found in the area ratio, the item is determined as "item with reduced pipe thickness" (step S324). Then, based on the area ratio, the deterioration level is determined (step S325). On the other hand, when no change is found in the area ratio, the item is determined as "no deterioration" (step S326).

Step S331: In the analysis in step S303, when a change is found in the decay time (reduction), the item is recognized as "item generated with axial crack." When the pipe to be inspected is recognized as "item generated with axial crack," the deterioration level is determined by means of maximum magnitude value analysis (step S332). Or, a resonant frequency spectrum chart (refer to FIG. 11) is created using the processing in steps S341 and S342; i.e., FFT. Then, the area ratio between the low frequency range and the high frequency range in the resonant frequency spectrum is calculated. Based on the area ratio, processing to determine the deterioration level is carried out.

Figure 21:
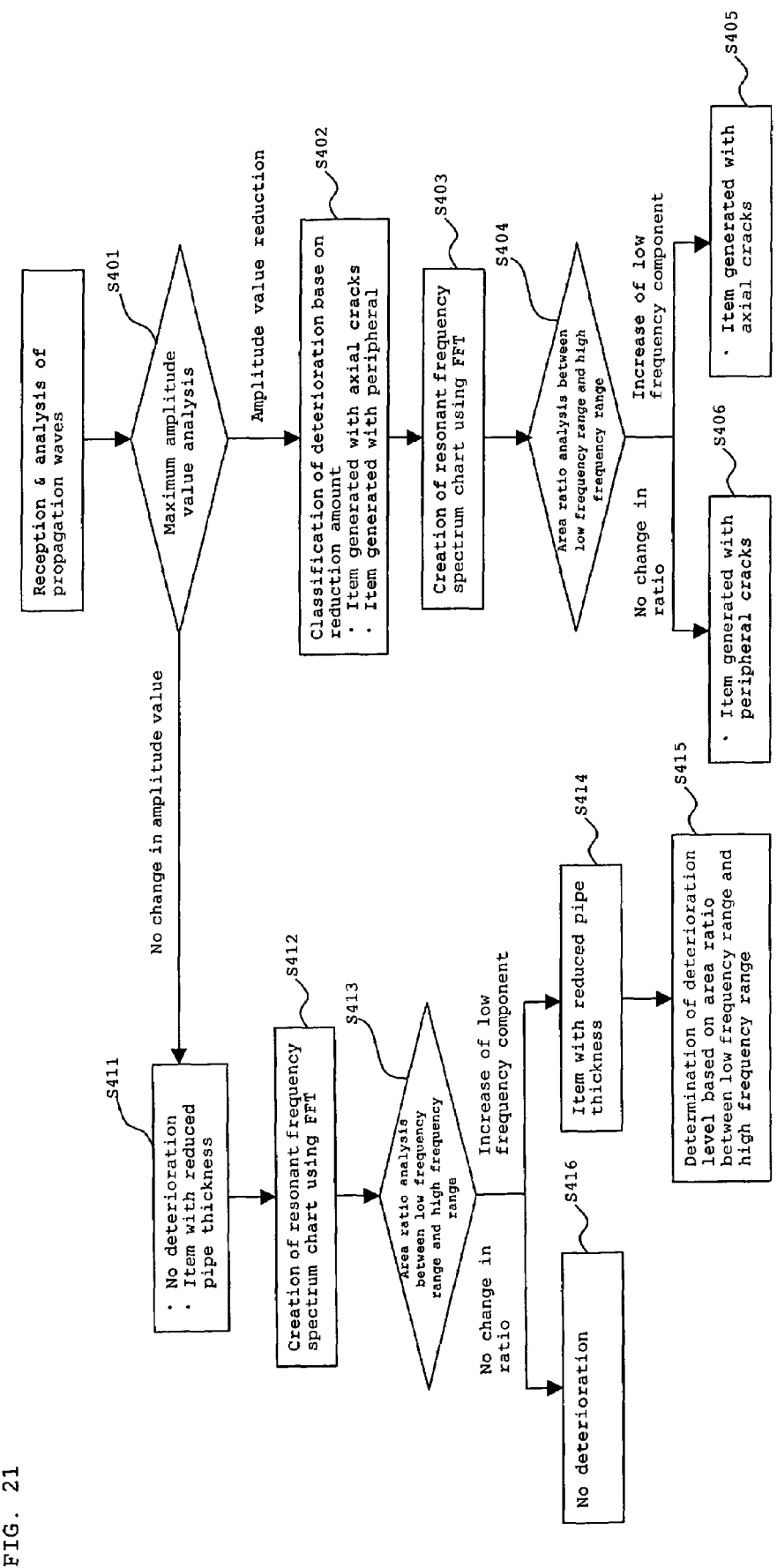
FIG. 21 is also a flowchart showing the steps in determination processing.

[Determination Processing J4: FIG. 21]

Step S401: Analysis of the maximum amplitude value in the propagation waves. When a change (reduction in amplitude) is found in the maximum amplitude value, the process proceeds to step S402. When no change is found in the maximum amplitude value, the process proceeds to step S411. The analysis of changes in the maximum amplitude value is made by comparison with a perfectly sound item.

Step S402: When a change is found in the maximum amplitude value of the propagation waves, the deterioration level is classified based on the reduced amount of the maximum amplitude value. When a change is found in the decay time and the maximum amplitude value of the propagation waves, the item is recognized as either or both of "item generated with axial crack" and "item generated with peripheral crack" (refer to Table 8).

Step S403: A resonant frequency spectrum chart (refer to FIG. 11) is created using FFT.

Step S404: The area ratio between the low frequency range and the high frequency range in the resonant frequency spectrum is analyzed (for analysis process, refer to the above Embodiment 2). When a change (increase of low frequency component) is found in the area ratio, the item is determined as "item generated with axial crack" (step S405). On the other hand, when no change is found in the area ratio, the item is determined as "item generated with peripheral crack" (step S406).

Step S411: In the analysis in step S401, when no change is found in the amplitude value, the item is recognized as "no deterioration" or "item with reduced pipe thickness" (refer to Table 8).

Step S412: A resonant frequency spectrum chart (refer to FIG. 11) is created using the FFT.

Step S413: The area ratio between the low frequency range and the high frequency range in the resonant frequency spectrum is analyzed (for a detailed analysis process, refer to Embodiment 2). When a change (increase of low frequency component) is found in the area ratio, the item is determined as "item with reduced pipe thickness" (step S414). Then, based on the area ratio, the deterioration level is determined (step S415). On the other hand, when no change is found in the area ratio, the item is determined as "no deterioration" (step S416).

Figure 22:
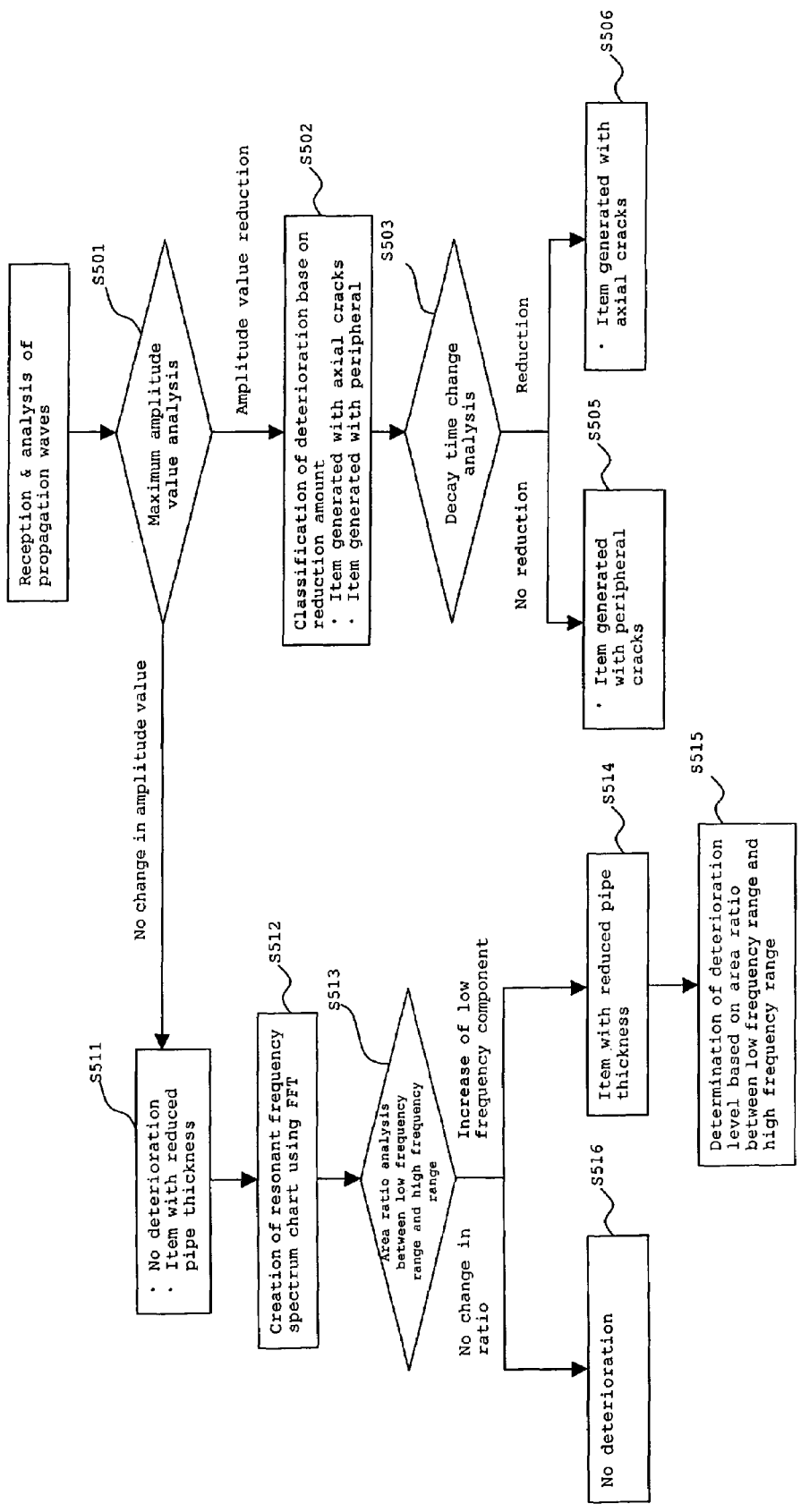
FIG. 22 is also a flowchart showing the steps in determination processing.

[Determination Processing J5: FIG. 22]

Step S501: Analysis of the maximum amplitude value in the propagation waves. When a change (reduction in amplitude) is found in the maximum amplitude value, the process proceeds to step S502. When no change is found in the maximum amplitude value, the process proceeds to step S511. The analysis of the change in maximum amplitude value is made by comparison with a perfectly sound item.

Step S502: When a change is found in the maximum amplitude value of the propagation waves, the deterioration level is classified based on the reduced amount of the maximum amplitude value. When a change is found in the decay time and the maximum amplitude value of the propagation waves, the item is recognized as either or both of "item generated with axial crack" or "item generated with peripheral crack" (refer to Table 8).

Step S503: Analysis of change in the decay time of the propagation waves. When a change (reduction in the decay time) is found in the decay time, the item is determined as "item generated with axial crack" (step S504). On the other hand, when no change is found in the decay time, the item is determined as "item generated with peripheral crack" (step S505).

Step S511: In the analysis in step S501, when no change is found in the amplitude value, the item is recognized as either or both of "no deterioration" or "item with reduced pipe thickness" (refer to Table 8).

Step S512: A resonant frequency spectrum chart (refer to FIG. 11) is created using the FFT.

Step S513: Analysis of area ratio between the low frequency range and the high frequency range in the resonant frequency spectrum (for analysis processing, refer to the above Embodiment 2). When a change (increase of low frequency component) is found in the area ratio, the item is determined as "item with reduced pipe thickness" (step S514). Then, the deterioration level is determined based on the area ratio (step S515). On the other hand, when no change is found in the area ratio, the item is determined as "no deterioration" (step S516).

EXAMPLE 5

A specific example of the present invention will be described.

[Sample Preparation]

The following samples were prepared using a product (inside diameter 250 mm) manufactured by Nippon Hume Corporation, conforming to JIS A 5303 type B, which were cut off as shown in FIG. 8.

Sample T51: non-processed item

Sample T52: item introduced with cracks

Item dropped on a concrete surface and generated with four cracks in the axial direction.

Sample T53: item introduced with cracks

Item dropped on concrete surface and generated with ten cracks in the axial direction (refer to FIG. 10). The number of the cracks in the samples T52 and T53, which were generated on the inner and outer surface, was visually checked at the one end surface thereof.

Sample T54: item introduced with peripheral cracks

Item generated with cracks with width of 0.15 mm in the peripheral direction by means of processing of crack introducing method shown in FIG. 13 (refer to FIG. 14).

Sample T55: item introduced with peripheral cracks

Item generated with cracks with width of 1.3 mm in the peripheral direction by means of processing of crack introducing method shown in FIG. 13 (refer to FIG. 14).

The width of cracks in the samples T54 and T55 were measured while being enlarged by a magnifier with a scale (average of values at 5 points).

Sample T56: pipe with ground inner surface

The reinforcing bars were exposed out of the inner surface layer by means of water jet blasting. Amount of grinding was set so as to be 1.6 mm in average grinding thickness. The ground amount was measured at ten points on each end in the area adjacent to the pipe end surface; total 20 points, using a slide caliper.

The list of samples is shown in Table 9.

[Injection and Receiving Position]

The injecting device and the receiving unit are disposed at the positions shown in FIG. 9, and injection of elastic waves and reception of propagation waves were performed.

[Used Apparatus]

Injecting device: P type Schmitt hammer

Receiver: a cylindrical item of a diameter of 10 mm, a height of 15 mm, was attached onto a male screw on a vibration sensor GH-313A (manufactured by Keyence Corporation). The receiver was set and held by hand.

Receiving amplifier: GA-245 (manufactured by Keyence Corporation)

Data logger (recording unit): NR-350 (manufactured by Keyence Corporation)

[Data Analysis]

(1) Determination of item with cracks: Based on the received waveform data, the maximum amplitude value (refer to FIG. 16) was calculated. The results are in Table 10.

As demonstrated in Table 10, based on the change in the maximum amplitude value, items with cracks can be sorted from others. Also, based on the change in maximum amplitude value, the progression level of the cracks can be determined.

(2) Determination of Reduction in Pipe Thickness

With respect to sample T51 and sample T56, using the waveform data of the obtained propagation waves, the resonant frequency spectrum was analyzed using an FFT analyzing program (manufactured by APTEC). Then, with respect to each of the respective resonant frequency spectrums, by dividing with 4 kHz as the boundary, the area ratio between the range of 0 to 4 kHz and the range of 4 to 8 kHz was obtained by Igor Pro (manufactured by Wave Metrics). The results are shown in FIG. 23.

Figure 23:
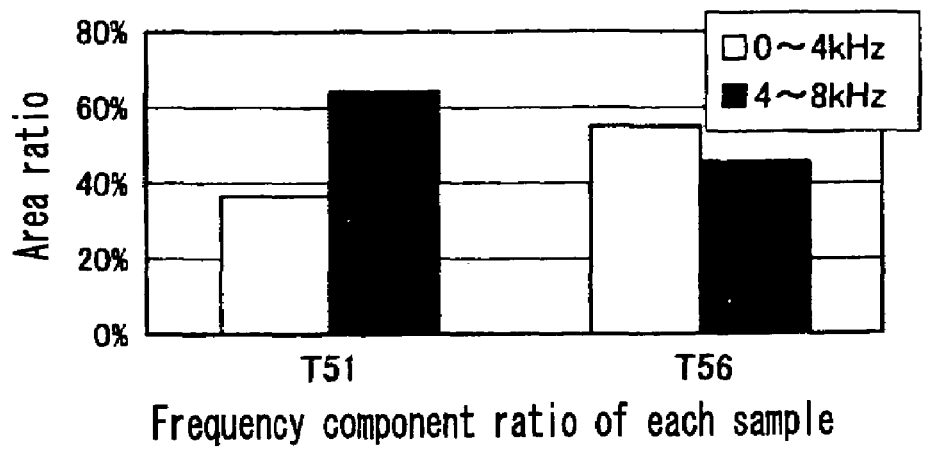
FIG. 23 is a graph showing the frequency component ratio of each sample.

As demonstrated in FIG. 23, it is possible to sort the item with reduced pipe thickness (sample T56) from the perfectly sound item. Based on the area ratio, the reduction level in the pipe thickness can be determined.

(3) Sorting of Crack Type

With respect to samples T52 to T56, using the waveform data of the obtained propagation waves, the resonant frequency spectrum was analyzed using the FFT function. Then, with respect to each of the resonant frequency spectrums, by dividing with 4 kHz as the boundary, the area ratio between the range of 0 to 4 kHz and the range of 4 to 8 kHz was obtained by Igor Pro (manufactured by Wave Metrics). The results are shown in FIG. 24.

Figure 24:
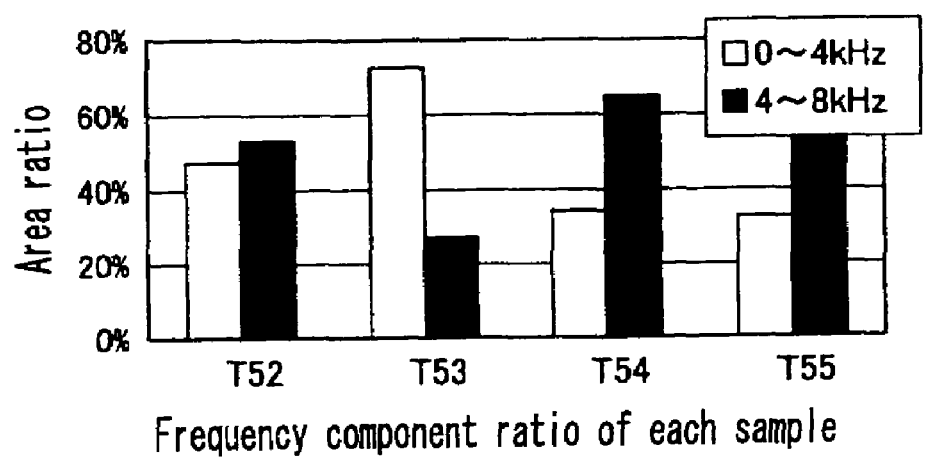
FIG. 24 is a graph showing the frequency component ratio of each sample.

As demonstrated in FIG. 24, in the case of the peripheral crack, no change is found in the area ratio. In the case of the axial crack, changes can be found in the area ratio. Accordingly, when a change is found in the area ratio, it can be determined that an axial crack is generated, and the type of cracks can be determined.

Further based on the comparison among the samples T51 to T53, the progress level of the axial cracks can be determined.

(4) Determination of the Progression Level of the Peripheral Cracks

With respect to the sample T54 and sample T55, using the waveform data of the received propagation waves, resonant frequency spectrums were obtained using the FFT function of the recording unit, and the respective resonant frequency spectrum charts were created. The resonant frequency spectrum of each sample is shown in FIGS. 25(a) and (b).

Figure 25A:
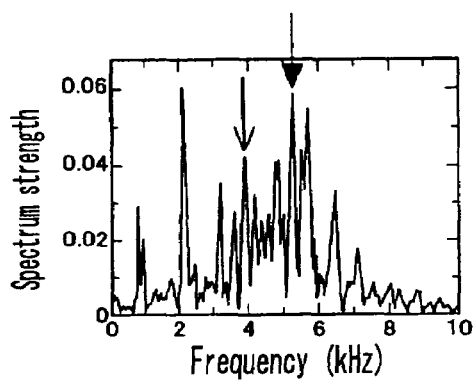
FIG. 25 are resonant frequency spectrum charts of each sample.
Figure 25B:
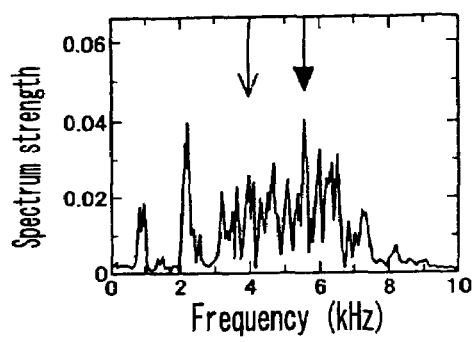

Then, with respect to each of the resonant frequency spectrums in FIGS. 25(a) and (b), top peak strength in the frequency range of 4 to 10 kHz (high frequency range) and the top peak strength in the frequency range of 3 to 4 kHz were obtained. And the strength ratio between the top peak strength in the frequency range of 4 to 10 kHz and the top peak strength of the frequency range (low frequency range) of 3 to 4 kHz was calculated. As a result, the strength ratio in the sample T54 was 1.40; and the strength ratio in the sample T55 was 1.64. As demonstrated in this result, based on the strength ratio between the top peak strength in the frequency range of 4 to 10 kHz and the top peak strength in the frequency range of 3 to 4 kHz in the resonant frequency spectrum, the progress level of the peripheral cracks can be determined. As described above, using the maximum amplitude value, the progress level can be determined.

Embodiment 6

Still another embodiment of the present invention will be described.

The injecting device and receiver used in the impact elastic wave test will be described first.

As for the injecting device, a hammering tool such as a hammer, a steel ball or an impulse hammer is available. In the impact elastic wave test, since it is preferred to carry out the hammering with the same force on a constant basis, for example, a method, in which the steel ball or the like is released with a specific force using a Schmitt hammer or a spring, or a method, in which the steel ball or the like is dropped from a specific height, is employed. Further, a method, in which hammering force of the impulse hammer is measured beforehand to take the influence of the hammering force into consideration during the data analysis, may be employed.

As for the receiver, an acceleration sensor, an AE sensor, vibration sensor or the like is available.

As for the setting method of the receiver, the receiver may be fixed using an adhesive tape or agent, or may be brought into contact with the object by hand, a holding tool or the like.

The injecting device and receiver may come into contact with water, acid water or basic water. Accordingly, the injecting device and receiver are preferably constituted of a material such as SUS, which is superior in anti-corrosion.

In this embodiment, an impact elastic wave test is carried out. That is, using a hammer, a steel ball or an impulse hammer, hammering is carried out on the inner surface at the end portion of the pipe to be inspected, propagated waves are detected with an acceleration sensor or a microphone set on the inner surface at the other end portion of the pipe to be inspected. Speed, decay time, magnitude, resonant frequency, phase and the like of the propagated wave are obtained. Based on the comparison with the perfectly sound item, the existence of deterioration is checked.

This embodiment is characterized in that, when reinforced concrete pipe constituting a sewage conduit or irrigation conduit is inspected by means of the impact elastic wave test, the distance between the elastic wave injecting position and the elastic wave receiving position is set being away from each other by ¼ or more of the length of the pipe to be inspected.

As described above, by carrying out the impact elastic wave test in a state that the distance between the elastic wave injecting position and the elastic wave receiving position is away from each other by ¼ or more of the length of the pipe, changes of the vibration mode of the entire reinforced concrete pipe due to aging can be detected easily resulting in an increased accuracy of the inspection.

EXAMPLE 6

A specific example of the present invention will be described.

[Sample Preparation]

The following samples were prepared using a product (inside diameter 2.50 mm) manufactured by Nippon Hume Corporation, conforming to JIS A 5303 type B, which were cut off as shown in FIG. 8.

Sample T61: non-processed item

Sample T62: item introduced with axial crack

Item dropped on concrete surface and generated with ten cracks in the axial direction (refer to FIG. 10). As for the number of cracks, number of cracks generated on the inner and outer surfaces was visually checked at one end surface. The number of the cracks in the samples T42 and T43, which were generated on the inner surface, was visually checked at the one end surface thereof.

[Injection and Receiving Position]

Figure 26:
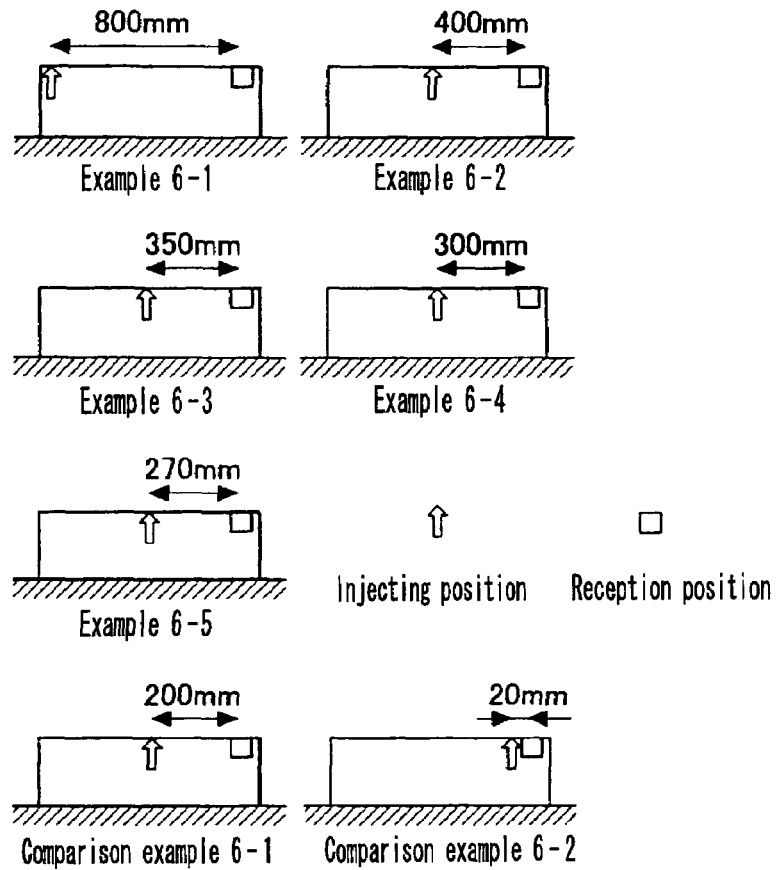
FIG. 26 are illustrations showing locations of a measuring device on a sample.

The injecting device and the receiving unit are disposed at the positions (Example 6-1 to 6-5 and Comparison example 6-1 and 6-2) shown in FIG. 26, and injection of elastic waves and reception of propagation waves were performed.

[Used Apparatus]

Injecting device: P type Schmitt hammer

Receiver: a cylindrical item (SUS) of a diameter of 10 mm, a height of 15 mm, was attached onto a male screw on a vibration sensor GH-313A (manufactured by Keyence Corporation). The receiver was set and held by hand.

Receiving amplifier: GA-245 (manufactured by Keyence Corporation)

Data logger (recording unit): NR-350 (manufactured by Keyence Corporation)

[Data Analysis]

Using the waveform data of the propagation waves received and recorded with the above apparatus, maximum amplitude values (refer to FIG. 16) of the respective samples were obtained. The result of the above is shown in Table 11 and FIG. 27.

Figure 27:
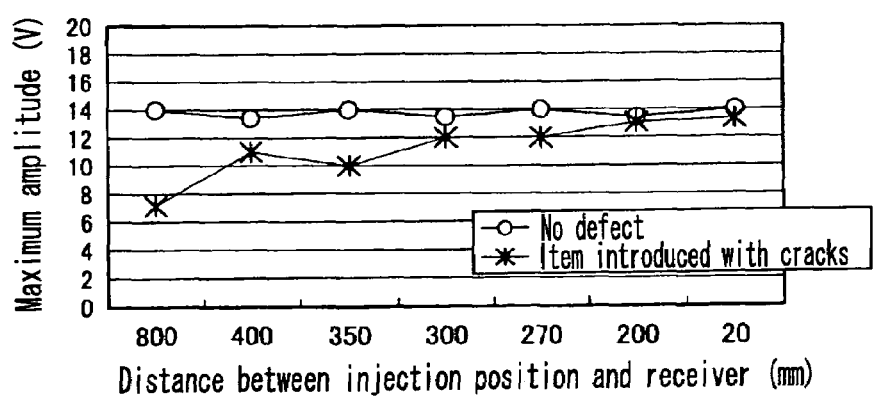
FIG. 27 is a graph showing the relationship between the incident position-receiver distance and the maximum amplitude value of a propagation wave.
Figures 28A, 28B, 28C, 28D, 28E:
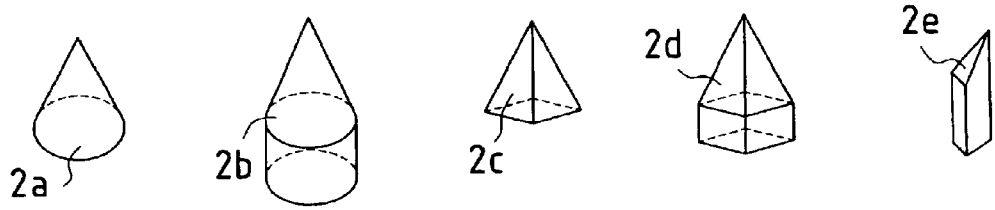
FIG. 28 are perspective views showing examples of receivers.
Figures 28F, 28G, 28H, 28I:
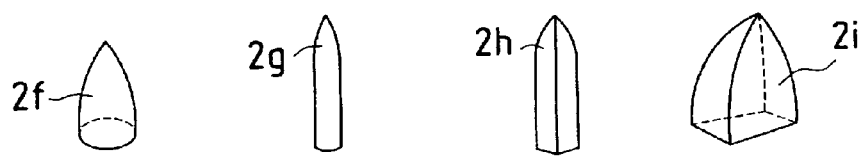
Figures 29A, 29B, 29C, 29D, 29E:
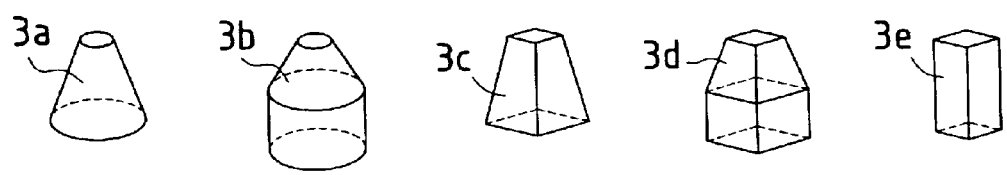
FIG. 29 are perspective views showing other examples of receivers.
Figures 29F, 29G, 29H, 29I:
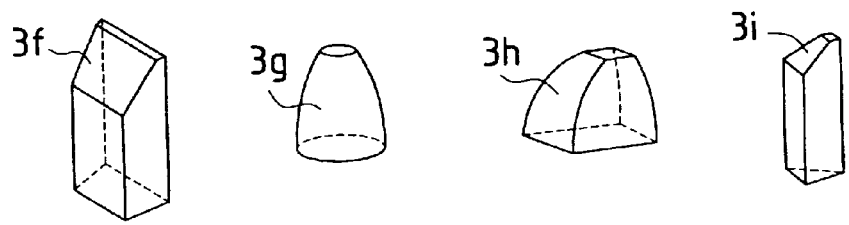
Figure 30A:
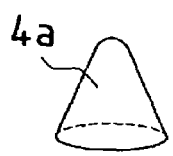
FIG. 30 are perspective views showing other examples of receivers.
Figure 30B:
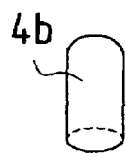
Figure 30C:
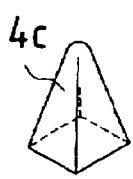
Figure 30D:
Figure 30E:
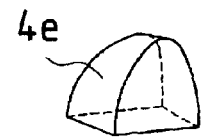
Figure 30F:
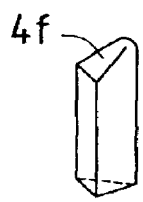
Figure 30G:
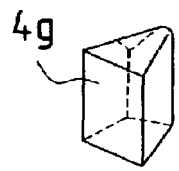

As demonstrated in Table 11 and FIG. 27, by setting the distance between the injecting device and the receiving unit (distance between the elastic wave injecting position and the elastic wave receiving position), ¼ or more (250 mm or more) of the length of the pipe to be inspected (1000 mm) away from each other, the generated cracks can be detected precisely.

Embodiment 7

In the present invention, as for the receiver used for the impact elastic wave test, as shown in FIGS. 28(a) to (e), receivers 2a-2e, which have the front end of a cone-like or pyramid-like shape, are available. In the case of a receiver of which the front end is a cone-like shape, as shown in FIGS. 28(f) to (i), receivers 2f to 2i, of which the conical surface (side surface) is formed into a curved surface, may be employed.

In place of a receiver having a cone-like shape as described above, a receiver of which the front end has a needle-like shape, may be employed.

As other examples of the receivers, as shown in FIGS. 29(a) to (i), receivers 3a to 3i, of which the front end surface is a flat-shape, are available. In the case of a receiver of which the front end surface is flat as described above, the area of the front end surface is 3 cm$^2$ or less, more preferably, 2.5 cm$^2$ or less. If the area of the front-end surface of the receiver is 3 cm$^2$ or more, the receiver fails to stably come into contact with the inner surface of the pipe to be inspected, and accordingly, the stability of the measurement is reduced.

As still other examples of receivers, as shown in FIG. 30(a) to (g), receivers 4a to 4g, of which the front end surface has a curved surface, are available. In the case of a receiver, of which the front end surface has a curved surface as described above, the curvature radius of the front end surface is preferably 25 mm or less, more preferably, 20 mm or less. If the curvature radius of the front end surface of the receiver is 25 mm or more, the receiver fails to stably come into contact with the inner surface of the pipe to be inspected, and accordingly, the stability of the measurement is reduced.

As for the setting method of the above-described receiver, the receiver may be fixed with an adhesive tape, agent or the like. The receiver may be held by hand, a holding tool or the like. Also, since the receiver may come into contact with water, acid water or basic water, the receiver is preferably made of a material such as SUS, which is superior in anti-corrosion.

EXAMPLE 7

A specific example of the present invention will be described.

[Sample Preparation]

The following samples were prepared using a product (inside diameter 250 mm) manufactured by Nippon Hume Corporation, conforming to JIS A 5303 type B, which were cut off as shown in FIG. 8.

Sample with reduced pipe thickness T71: The reinforcing bars were exposed out of the inner surface layer by means of water jet blasting. Amount of grinding was set so as to be 1.6 mm in average grinding thickness. The ground amount was measured at ten points on each end surface in an area adjacent to the pipe end; total 20 points, using a slide caliper.

Sample applied with lard T72: item applied with lard on the inner surface of the pipe. Average thickness of the lard is approximately 1 to 4 mm.

[Injection and Receiving Position]

The injecting device and the receiving unit were disposed at the positions shown in FIG. 9, and injection of the elastic waves and the reception of the propagation waves were carried out.

[Used Apparatus]

Injecting device: P Type Schmitt hammer

Receiver: a cylindrical item (receiver) having a configuration shown in FIG. 31 was attached onto a male screw on a vibration sensor GH-313A (manufactured by Keyence Corporation). The receiver was set and held by hand.

Receiving amplifier: GA-245 (manufactured by Keyence Corporation)

Data logger (recording unit): NR-350 (manufactured by Keyence Corporation)

[Measurement Result]

Using receivers (Examples 7-1 to 7-3 and Comparison examples 7-1) shown in FIG. 31, the impact elastic wave test was carried out three times each, and the difference among the maximum amplitude values was examined. The results are in Table 12 and FIG. 32.

Figure 32A:
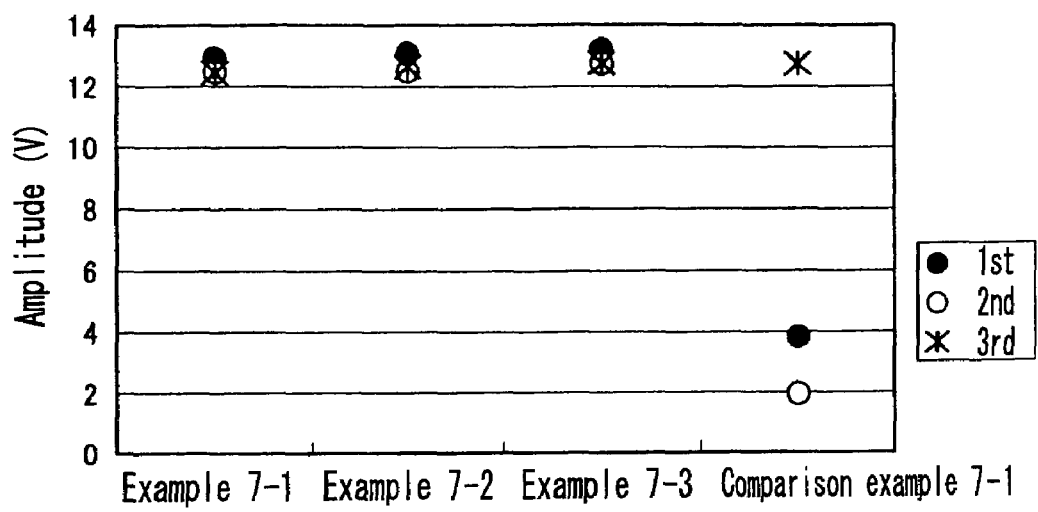
FIG. 32 are graphs showing measurement results of examples of the present invention.
Figure 32B:
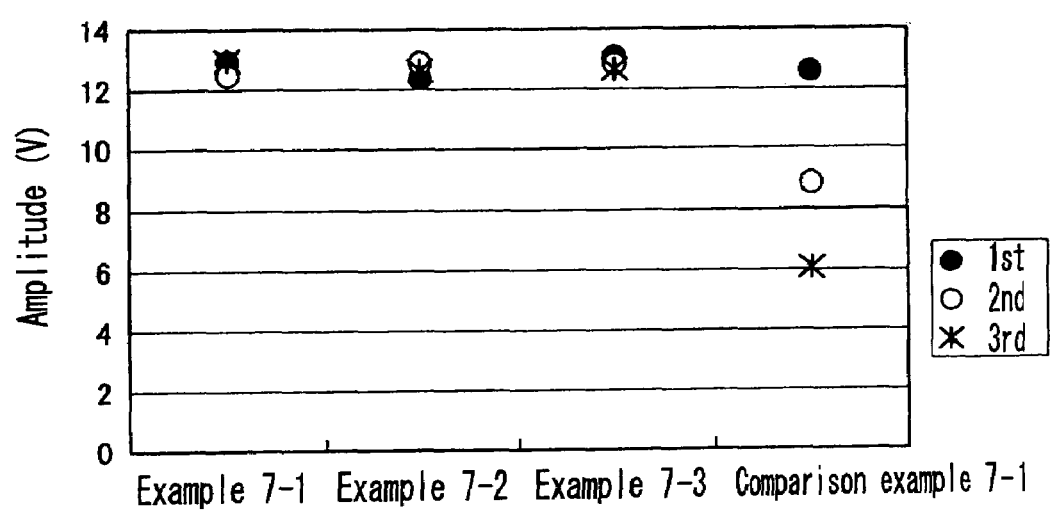

As demonstrated in the results shown in the above Table 12 and FIG. 32, by controlling the configuration of the receiver, the inspection using the impact elastic waves can be performed for accurate measurement.

Embodiment 8

Figure 33:
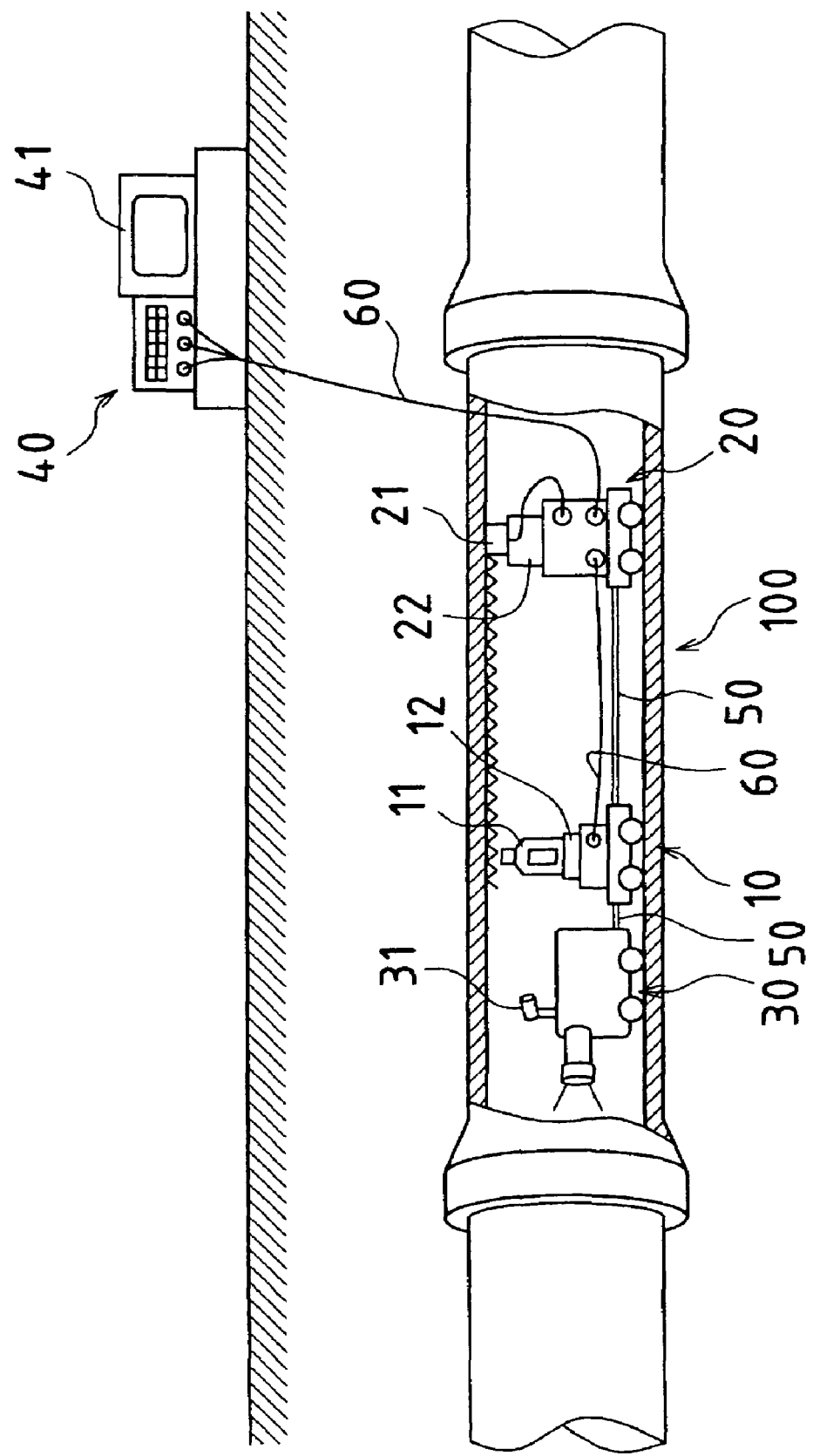
FIG. 33 is a view schematically showing a configuration of an embodiment of an inspection apparatus according to the present invention.

Referring to FIG. 33, an embodiment of an inspection apparatus for reinforced concrete pipes according to the present invention will be described.

An inspection apparatus shown in FIG. 33 comprises a hammering unit trolley 10, a receiving unit trolley 20, a TV camera trolley 30 and a data recording unit 40. The hammering unit trolley 10, the receiving unit trolley 20 and the TV camera trolley 30 are capable of traveling inside a Hume pipe 100, which is a pipe to be inspected. The data-recording unit 40 is disposed above ground within an area to be inspected.

The hammering unit trolley 10 and the receiving unit trolley 20 are connected to each other with a joint member 50, and it is arranged so that influence due to vibration generated from the hammering unit trolley 10 at hammering is not rendered to the receiving unit trolley 20 side.

It is preferred that the inspection apparatus and the joint 50 are made of materials such as stainless steel and aluminum alloy, which hardly accumulate rust, and are provided with waterproofing characteristic.

As for the connecting method between the joint member 50 and the hammering unit trolley 10 and the receiving unit trolley 20, for example, the following method may be employed. That is, a connecting female screw (not shown) is provided to each of the trolleys 10 and 20, and on the both ends of the joint member 50, a male screw (not shown), which is coupled with the connecting female screw on each of the trolleys 10 and 20 is prepared respectively, and the male screw at the end portion of the joint member 50 is screwed into the connecting female screw on each of the trolleys 10 and 20 to connect to each other.

Also, as another connecting method, an eye bolt is provided to each of the trolleys 10 and 20, a hook is provided to both end portions of the joint member 50, and each of the hooks is hooked to each of the eye bolts on the trolleys 10 and 20 to connect to each other.

Since the distance between the hammering unit trolley 10 and the receiving unit trolley 20 has to be maintained at a specific distance, the joint member 50 is made of, for example, a material such as metal or resin, which hardly expands and contracts.

The hammering unit trolley 10 and the receiving unit trolley 20 are connected to each other via an electric cable 60 for data transfer. Also, the receiving unit trolley 20 is connected to the data-recording unit 40 above ground via the electric cable for data transfer 60.

Mounted on the hammering unit trolley 10 is an injecting device 11 of an elastic wave. The injecting device 11 is disposed on a lifting mechanism 12, which is provided with a driving force by means of electric power or an air cylinder. Being driven by the lifting mechanism 12, the injecting device 11 can be moved to a position where the hammering is possible at measurement. Also, the injecting device 11 can be moved to a position where the injecting device 11 is free from coming into contact with the inner surface of the pipe during traveling.

Mounted on the receiving unit trolley 20 is a receiving unit 21 for receiving the propagated wave. The receiving unit 21 is disposed on a lifting mechanism 22 and provided with a driving force such as electric power or air cylinder. Being driven by the lifting mechanism 22, the receiving unit 21 can be raised to a position where the reception is possible at measurement. Also, the receiving unit 21 can be lowered to a position where the receiving unit 21 is free from coming into contact with the inner surface of the pipe during traveling.

The above-mentioned apparatuses such as injecting device 11 and the receiving unit 21 are securely fixed to each of the trolleys 10 and 20 with bolts or the like.

A CCD camera 31 mounted on the TV camera trolley 30 is used for determining the elastic wave injecting position by the injecting device 11, the elastic wave receiving position by the receiving unit 21 and the receiving position. The image data from the CCD camera 31 are guided to the data-recording unit 40 via an electric cable for data transfer (not shown), and displayed on a screen of a monitor 41.

In the embodiment shown in FIG. 33, an example, in which the CCD camera 31 is mounted on the TV camera trolley 30, is shown; but it is limited thereto. The CCD camera may be mounted on any one or both of the hammering unit trolley 10 and the receiving unit trolley 20. Further, it is preferred to mount a lighting apparatus the same as the CCD camera 31 for facilitating confirmation of the observation point.

The CCD camera also travels inside the existing conduit. Identical to the above-described inspection apparatuses and the like, a waterproofing characteristic is preferably provided to the CCD camera.

As for the traveling means of the hammering unit trolley 10, the receiving unit trolley 20 and the TV camera trolley 30 within the conduit, the following methods are conceivable. That is, the TV camera trolley 30 or the receiving unit trolley 20, which is positioned at the top, is pulled with a wire or the like; or, the TV camera trolley 30 or the receiving unit trolley 20 is arranged so as to be self-driven to travel.

Further, it is preferred that, in the hammering unit trolley 10, the distance from the top of the pipe to the hammering point is maintained at a fixed distance to stabilize the hammering force provided to the object to be measured; and thus, to increase the accuracy of the obtained data.

In the embodiment shown in FIG. 33, in the receiving unit trolley 20, the lifting mechanism 22 and the receiving unit 21 are mounted in this order on the measuring apparatus main body. However, it is preferred that, for example, a control mechanism such as a load cell, which is capable of controlling the contact force of the receiving unit 21, is mounted inside the lifting mechanism 22. Thereby, a constant contact force can be obtained during measurement resulting in an increased accuracy of the obtained data.

Owing to the inspection apparatus having the above-described structure, even when a reinforced concrete pipe of a small diameter into which an inspector cannot enter is inspected, the impact elastic wave test can be readily carried out.

Here, in the inspection apparatus of the embodiment, by changing (1) the lifting mechanism, (2) the wheel diameter of the trolleys and/or (3) the size of the trolley, the inspection apparatus of the embodiment can be applied to the inspection of pipes to be inspected each having a different pipe diameter. Further, by adjusting the length of the joint member 50, the inspection apparatus of the embodiment can be applied to the inspection of pipes to be inspected each having a different length of pipe.

In the embodiment shown in FIG. 33, an example, in which the data recording unit is disposed above ground, is shown; but is not limited thereto. The data-recording unit may be mounted on the hammering unit trolley or the receiving unit trolley.

INDUSTRIAL APPLICABILITY

As described above, according to the inspection method of the present invention, when inspecting the deterioration state of a reinforced concrete pipe constituting a sewage conduit, an irrigation conduit or the like, the progression level of the deterioration in a component segment of an area to be inspected is classified, and a portion to be inspected in detail is selected. Accordingly, the time for inspection work can be reduced. Also, the progression level of the deterioration in the portion to be inspected in detail can be evaluated quantitatively based on the strength of the pipe. Further, since the magnitude of the progression level of deterioration can be evaluated quantitatively, based on the strength of the pipe in the portion to be inspected in detail, the strength of the pipe in each of the component segments can be estimated.

In the inspection method according to the present invention, by arranging to carry out the determination using various data of deterioration phenomena such as the area ratio between the high frequency component and the low frequency component in a resonant frequency spectrum of propagation waves, the top peak strength ratio between a frequency range of 4 to 10 kHz and a frequency range of 3 to 4 kHz in the resonant frequency spectrum of the propagation waves, the maximum amplitude value of the propagation waves and decay time of the propagation waves and the like, the deterioration level of the reinforced concrete pipe constituting the sewage conduit, irrigation conduit and the like can be determined quantitatively. Further, by arranging to carry out the determination while combining those data of deterioration phenomena, classification of major deterioration phenomena such as axial cracks, peripheral cracks and reduction in thickness of the reinforced concrete pipe and the determination of the progression level of the deterioration can be carried out quantitatively.

In the inspection method according to the present invention, by carrying out the impact elastic wave test in a state in which the distance between the elastic wave injecting position and the elastic wave receiving position is ¼ or more of the length of the pipe to be inspected away from each other, the changes of vibration mode due to the deterioration can be detected precisely.

In the inspection method according to the present invention, by carrying out the impact elastic wave test using a receiver of which the front end is a cone-like shape or needle-like shape, a receiver of which front end surface is flat and the area of the front end surface is 3 cm$^2$ or less, or a receiver of which the front end surface is a curved surface and the curvature radius of the front end surface thereof is 25 mm or less as the receiver of the elastic waves, the inspection by means of the impact elastic wave test can be carried out accurately irrespective of the state of the inner surface layer of the pipe to be inspected.

According to the inspection apparatus of the present invention, even when inspecting a reinforced concrete pipe having such a small diameter that an inspector or the like cannot enter thereinto, the inspection method having features as described above can be carried out readily.

TABLE 1

| Sample | Resonant frequency | Classification of deterioration |
|---|---|---|
| T11 | 0.8 KHz | 3 |
| T12 | 0.2 KHz | 1 |
| T13 | 0.5 KHz | 2 |

TABLE 2

| Sample T21 | Sample T22 | Sample T23 | Sample T24 |
|---|---|---|---|
| Non-processed item | Item introduced with 4 axial cracks | Item introduced with 10 axial cracks | Pipe with ground inner surface |

TABLE 3

Area ratio calculation result of each sample

| | Sample | | | |
|---|---|---|---|---|
| | T21 | T22 | T23 | T24 |
| 0 to 4 KHz | 32% | 47% | 73% | 55% |
| 4 to 8 KHz | 68% | 53% | 27% | 45% |

TABLE 4

| Sample T31 | Sample T32 | Sample T33 |
|---|---|---|
| Non-processed item | Item introduced with peripheral crack: 0.15 mm | Item introduced with peripheral crack: 1.3 mm |

TABLE 5

Peak strength ratio calculation result

| | Sample | | |
|---|---|---|---|
| | T31 | T32 | T33 |
| Peak strength ratio | 0.97 | 1.40 | 1.57 |

TABLE 6

| Sample T41 | Sample T42 | Sample T43 | Sample T44 | Sample T45 |
|---|---|---|---|---|
| Non-processed item | Item introduced with 4 axial cracks | Item introduced with 10 axial cracks | Item introduced with peripheral crack: 0.15 mm | Item introduced with peripheral crack 1.3 mm |

TABLE 7

Maximum amplitude value (output value of receiving unit [v]) of each sample

| Sample T41 | Sample T42 | Sample T43 | Sample T44 | Sample T45 |
|---|---|---|---|---|
| 14.0 | 10.8 | 7.1 | 11.0 | 8.3 |

TABLE 8

| Deterioration phenomena | Pipe with reduced thickness | Peripheral crack | Axial crack |
|---|---|---|---|
| Maximum amplitude value | No change | Reduction | Reduction |
| Decay time | No change | No change | Reduction |
| Area ratio between an area of high frequency component and an area of low frequency component | High frequency component is reduced. | No change | High frequency component is reduced. |
| Top peak strength in the frequency range of 4 to 10 KHz and top peak strength in the frequency range of 3 to 4 kHz | Strength in the low frequency side is small. | Strength in the high frequency side is large. | No change |

TABLE 9

| Sample T51 | Sample T52 | Sample T53 | Sample T54 | Sample T55 | Sample T56 |
|---|---|---|---|---|---|
| Non-processed item | Item introduced with 4 axial cracks | Item introduced with 10 axial cracks | Item introduced with peripheral crack: 0.15 mm | Item introduced with peripheral crack 1.3 mm | Pipe with ground inner surface |

TABLE 10

Maximum amplitude value (output value of receiving unit [v]) of each sample

| Sample T51 | Sample T52 | Sample T53 | Sample T54 | Sample T55 | Sample T56 |
|---|---|---|---|---|---|
| 14.0 | 10.8 | 7.0 | 11.0 | 8.3 | 13.8 |

TABLE 11

| | Example 6-1 | Example 6-2 | Example 6-3 | Example 6-4 | Example 6-5 | Comparison example 6-1 | Comparison example 6-2 |
|---|---|---|---|---|---|---|---|
| Distance between the injection and the reception (mm) | 800 | 400 | 350 | 300 | 270 | 200 | 20 |
| No deterioration | 14.0 | 13.5 | 14.0 | 13.5 | 14.0 | 13.5 | 13.9 |
| Item introduced with crack | 7.1 | 11.0 | 10.0 | 11.9 | 12.0 | 13.1 | 13.5 |

TABLE 12

| | Example 7-1 | Example 7-2 | Example 7-3 | Comparison example 7-1 |
|---|---|---|---|---|
| (a) Measurement results of sample with reduced pipe thickness | | | | |
| 1st | 12.83 | 13.03 | 13.13 | 3.81 |
| 2nd | 12.53 | 12.53 | 12.73 | 1.90 |
| 3rd | 12.53 | 12.73 | 12.83 | 12.73 |
| (b) Measurement results of sample applied with lard | | | | |
| 1st | 12.79 | 12.45 | 12.98 | 12.56 |
| 2nd | 12.56 | 12.78 | 12.78 | 11.79 |
| 3rd | 12.91 | 12.56 | 12.63 | 6.12 |

What is claimed is:

1. An inspection method for reinforced concrete pipes for inspecting the deterioration state of a reinforced concrete pipe inside the pipe, comprising the steps of:

measuring propagation waves of a pipe to be inspected by carrying out an impact elastic wave test;

analyzing the resonant frequency spectrum of the propagation waves; and determining the deterioration level based on the area ratio between an area of a high frequency component and an area of a low frequency component in the resonant frequency spectrum.

* * * * *